United States Patent
Hoffman et al.

Patent Number: 5,912,341
Date of Patent: Jun. 15, 1999

[54] HETEROATOM-FUNCTIONALIZED PORPHYRAZINES AND MULTIMETALLIC COMPLEXES AND POLYMERS DERIVED THEREFROM

[75] Inventors: Brian M. Hoffman, Evanston, Ill.; Anthony G.M. Barrett, London, United Kingdom

[73] Assignee: Hoffman/Barrett, L.L.C., Evanston, Ill.

[21] Appl. No.: 08/928,415

[22] Filed: Sep. 12, 1997

Related U.S. Application Data

[63] Continuation-in-part of application No. 08/403,302, Mar. 14, 1995, Pat. No. 5,675,001.

[51] Int. Cl.[6] ............... C07D 487/22; C09B 47/00; C09B 47/04; C09B 62/00
[52] U.S. Cl. ............... 540/121; 540/122; 540/139; 540/140; 540/145
[58] Field of Search ............... 540/121, 122, 540/139, 140, 145

[56] References Cited

U.S. PATENT DOCUMENTS 5,675,001  10/1997  Hoffmann et al. ............... 540/121

OTHER PUBLICATIONS

Elvridge et al., "Conjugated Macrocycles, Part XXVII, The Formation of Tetrazaporphins from Imidines," Tribenzotetrazaporphin, *J. Chem. Soc.*, pp. 3536–3544, 1955.

Kopranenkov et al., "Phthalocyanines and Related Compounds," *Journal of Organic Chemistry of the USSR*, 15:5, Part 2, pp. 962–967, May, 1979.

Schramm et al., "Octakis(alkylthio)tetraazaporphyrins," *Inorg. Chem.*, 19, pp. 383–385, 1980.

Velazquez et al., "Metal–Encapsulated Prophyrazines: Synthesis X–ray Crystal Structure, and Spectroscopy of a Tetrain–star–Ni(porphyrazine)$S_8$ Complex;" *J. Am. Chem. Soc.*, 112:20, pp. 7408–7410, 1990.

Velazquez et al. "star–Porphyrazines: Synthetic, Structural, and Spectral Investigation of Complexes of the Polynucleating Porphyrazineoctathiolato Ligand," *J. Am. Chem. Soc.*, 114, pp. 7416–7424, 1992.

Velazuez et al., "Star Porphyrazines: Peripheral Chelation of Porphyrazineoctathiolate by Diphosphinonickel Ions," *J. Am. Chem. Soc.*, 115, pp. 9997–10003, 1993.

Mani et al., Synthesis and Characterisation of Porphyrazinoctamine Derivates: X–Ray Crystallographic Studies of [2,3,7,8,12,13,17,18–Octakis(dibenzylamino)–porphyrazinato]magnesium (II) and {2,3,7,8,12,13,17,18–Octakis[allyl(benzyl)–amino]–porphyrazinato}Nickel (II), *J. Chem. Soc., Chem. Commun.*, pp. 2095–2096, 1994.

Baumann et al., "Solitaire Porphyrazines: X–Ray Crystal Structure and Spectroscopy of [1,1'–Bis(diphenylphosphino)ferrocene]–[(norphthalocyanine)dithiolato]–palladium(II), " *J. Am. Chem. Soc.*, 116, pp. 2639–2640, 1994.

Mani et al., "Serendipitous Desymmetrisation during Porphyrazine Synthesis: an X–Ray Crystallographic Study of 2,3,7,8,12,13,17, 18–Octakis(dimethylamino)–2–secoporphyrazine–2,3–dione," *Journal of the Chemical Society* 17, pp. 1943–1944 (1994).

*Primary Examiner*—Nathan M. Nutter
*Attorney, Agent, or Firm*—Marshall, O'Toole, Gerstein, Murray & Borun

[57] ABSTRACT

Porphyrazine compounds having moieties substituted at the eight peripheral β-pyrrole positions are disclosed. The porphyrazine compounds have the general structural formula:

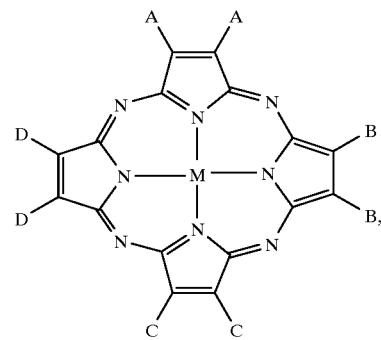

wherein M is $H_2$ or a metal capable of complexing with the pyrrole nitrogen atoms, and A, B, C, and D are independently selected from the group consisting of a thio moiety, an amino moiety, an oxo moiety, a phospho moiety, a seleno moiety, a telluro moiety and a noncoordinating moiety, like a hydrocarbon moiety, with the proviso that not all of A, B, C, and D are a thio moiety and that not all of A, B, C, and D are a hydrocarbon moiety. The porphyrazine compounds, depending on the identity of A, B, C, and D, are capable of complexing one to four metal ions to the periphery of the porphyrazine to form a multimetallic porphyrazine. Multimetallic porphyrazine compounds can be linked peripherally to form a linear, i.e., ribbon, polymer or a two-dimension, i.e., sheet polymer. The porphyrazine compounds, and the multimetallic complexes and polymers derived therefrom, are useful in, or as, magnet materials, molecular metal conductors, pharmaceuticals, imaging agents, and dyes.

32 Claims, No Drawings

HETEROATOM-FUNCTIONALIZED PORPHYRAZINES AND MULTIMETALLIC COMPLEXES AND POLYMERS DERIVED THEREFROM

CROSS REFERENCE TO RELATED APPLICATIONS

This is a continuation-in-part application of U.S. patent application Ser. No. 08/403,302, filed Mar. 14, 1995, and now U.S. Pat. No. 5,675,001.

This invention was made with government support under grant numbers DMR-9119832, CHE-9107589, and CHE-9408561 awarded by the National Science Foundation. The government may have certain rights in this invention.

FIELD OF THE INVENTION

The present invention relates to macrocyclic porphyrazine compounds regioselectively functionalized with heteroatom moieties at the periphery of the compound. The porphyrazine compounds are capable of complexing up to five metal ions to form multimetallic porphyrazine compounds. The present invention also relates to oligomers and polymers derived from the multimetallic porphyrazine compounds. More particularly, the present invention relates to porphyrazine compounds having heteroatom moieties selectively positioned at the eight peripheral β-pyrrole positions, such that the porphyrazines are capable of complexing up to four metal ions to the periphery of the porphyrazine, in addition to complexing one element within the macrocyclic cavity. The resulting multimetallic porphyrazine compounds can be formed into oligomers or polymers through linkages provided by the peripherally complexed metal ions. The porphyrazine compounds, and the multimetallic porphyrazine compounds, oligomers, and polymers, have applications as magnetic materials, molecular metal conductors, pharmaceuticals, imaging agents, and dyes.

BACKGROUND OF THE INVENTION

Advances in the chemistry and practical applications of metal-organic compounds relies on the development of new ligand systems. For example, advances in the development of catalysts for asymmetric organic synthesis and carbon-hydrogen activation; models for active sites of metalloproteins; crown ethers, cryptands, and spherands for the selective complexation of closed-shell cations; high-affinity ligands for transition metals; and oxygen transport and storage systems are attributable to new ligand systems.

Numerous phthalocyanine (i.e., tetrabenzoporphyrazine) and porphyrazine (i.e., tetraazaporphyrin) compounds have been formed by complexing different elements within the macrocyclic cavity of these compounds, i.e., the two hydrogen atoms within the cavity are replaced by an element, such as a metal ion or metalloid. The resulting coordination compounds are widely used in industry as dyes and colorants, as oxidation catalysts and as photoconductors.

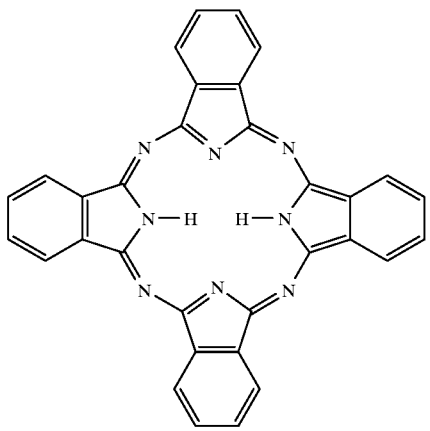

phthalocyanine

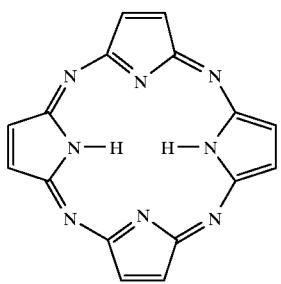

porphyrazine

Polymeric phthalocyanines also are known. For example, 1,2,4,5-benzenetetranitrile, 1,4-bis-(3,4-dicyanophenoxy)benzene, and, 1,4'-bis(3,4-dicyanophenoxy) biphenyl each have been incorporated into polymeric phthalocyanines by crossover macrocyclization in a reaction with other 1,2-dinitriles. Cross-over macrocyclization is disclosed in J. Elvridge et al., J. Chem. Soc., page 3536 et seq. (1955), incorporated herein by reference and referred to herein as the Linstead macrocyclization procedure.

These polymerization reactions typically provided complex, nonhomogeneous polymers of ill-defined structure. For example, the preparation of polymeric phthalocyanines by the well-known Linstead macrocyclization procedure is complicated by undesirable side reactions which lead to the formation iminoindoline, carboxamide, carboxylic acid and s-triazine by-products. In addition, the formation of various isomers is an additional disadvantage that increases in significance as the molecular weight of an oligophthalocyanine increases. Furthermore, many of the polymeric phthalocyanines are highly insoluble in organic solvents, thereby precluding purification, characterization, and, ultimately, manufacture, fabrication, and practical application.

Alternative routes for preparing polymeric phthalocyanines exist. For example, phthalocyanine tetracarboxylic acids and tetraamines have been polymerized via the formation of amides or benzimidazoles. Methacrylate-substituted phthalocyanine compounds have been polymerized by free radical techniques, and various polymers having halide substituents have been functionalized with phthalocyanines having amino groups. Arrays of cofacially stacked phthalocyanines also have been assembled by linking metallophthalocyanines via shared axial ligands.

Notwithstanding the previous work with respect to phthalocyanines and polymeric phthalocyanines, there still is a need in the art for novel phthalocyanine or porphyrazine compounds, and polymers derived therefrom, that are easy to manufacture, that are of defined structure, and that can be designed to exhibit predetermined properties such as color, solubility, conductivity, and magnetic moment. The preparation of such porphyrazine-based polymers first requires the development and synthesis of suitably substituted porphyrazine compounds to act as monomers or precursors.

The present invention, therefore, is directed to porphyrazine compounds which can be selectively functionalized at the periphery with up to eight heteroatom moieties, either the same or different, for their intrinsic properties. The porphyrazine compounds have the inherent capability of complexing one element (M) within the center of the molecule (i.e., the macrocyclic cavity), and, if desired, can have the further capability of complexing one, two, three or four additional metal ions ($M^1$), either the same or different, to the periphery of the porphyrazine compound. The resulting multimetallic porphyrazine compounds then are used to prepare porphyrazine oligomers or polymers by edge-sharing the peripherally complexed $M^1$ metal ions between adjacent multimetallic porphyrazine compounds, as illustrated by the porphyrazine oligomer of structural formula I, wherein two metalloporphyrazine monomers are linked by an edge-shared, peripherally complexed octahedral metal ion $M^1$.

identity of the noncoordinating Y moiety, a broad range of novel multimetallic porphyrazine compounds, oligomers, and polymers can be prepared.

The present porphyrazine compounds provide multimetallic porphyrazines and porphyrazine-based oligomers and polymers that are distinct from, and have superior properties over, existing porphyrazine and phthalocyanine compounds, and oligomers and polymers derived therefrom. The improved properties result, in part, from direct contact between the peripheral heteroatom moieties and the pi ($\pi$) system of the porphyrazine macrocycle, the ability to control physical and chemical properties of the compounds by a judicious selection of the type and number of heteroatomic moieties, and their geometric relation at the periphery of the compound. The peripherally complexed $M^1$ metal ions interact with the pi ($\pi$) system of the porphyrazine macrocycle to provide a varied metal to metal (i.e., M to $M^1$) communication which is manifested by charge and spin delocalization, the formation of high spin molecules, and multi-level redox chemistry. Such properties form the basis of new colorants, new imaging agents, and improved magnetic materials and conductors. Additionally, porphyrazine oligomerization via peripherally complexed $M^1$ metal ions provides, in many cases, homogeneous polymers of known structure and predetermined molecular weight.

In addition to multimetallic, porphyrazine-based oligomeric and polymeric compounds, multimetallic complexes

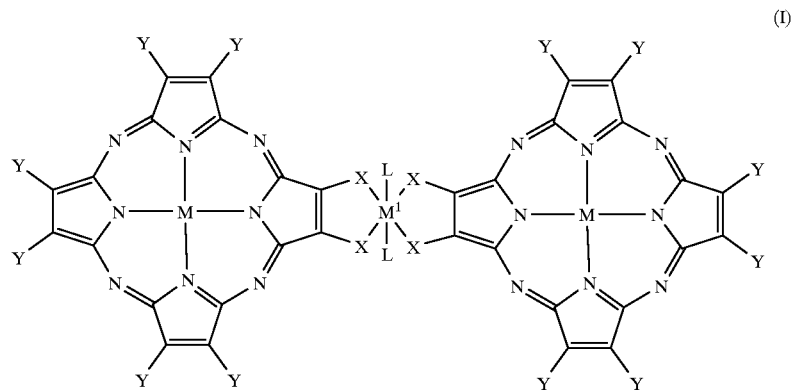

(I)

In porphyrazine oligomer I, M is 2H or is an element (e.g., a metal ion or a metalloid) capable of being complexed within the macrocyclic cavity, $M^1$ is a metal ion capable of complexing with the moiety X, X is a moiety having sulfur, oxygen, nitrogen, phosphorus, selenium or tellurium atoms for complexing with $M^1$, Y is a noncoordinating moiety, e.g., a hydrocarbon moiety (including hydrogen) or any other moiety that is incapable of coordinating with an $M^1$ metal ion, and L is a ligand that completes the coordination sphere of $M^1$. By appropriate choice of element M and metal ion $M^1$, by varying the number and identity of peripheral moieties X (i.e., having more than two X moieties per porphyrazine compound, such as four, six or eight X moieties), by changing the identity of ligands L that complete the coordination sphere of the peripherally complexed $M^1$ metal ions, by changing the coordination sphere of the peripherally complexed $M^1$ metal ions, and by varying the prepared from a porphyrazine capable of complexing with multiple metal ions are important in the fields of electron transfer, magnetic interactions, optical phenomena, excited-state reactivity, biomimetic chemistry, mixed valency and ionophoric activity. Investigators previously have studied polynucleating macrocyclic ligands, and in particular have studied some porphyrins and phthalocyanines functionalized with moieties capable of coordinating with metal ions.

For example, porphyrazine compounds having all sulfur or all hydrocarbon moieties positioned at the eight peripheral β-pyrrole positions have been prepared. The synthesis of porphyrazine-2,3,7,8,12,13,17,18-octathiolate, depicted as the compound of structural formula II, has been reported by Velazquez et al. in *J. Am. Chem. Soc.*, 115, pages 9997–10003 (1993).

(II)

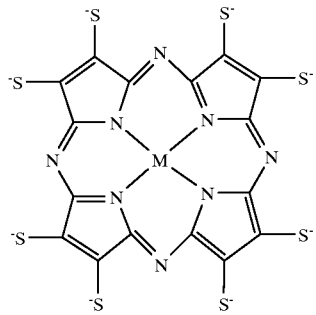

-continued

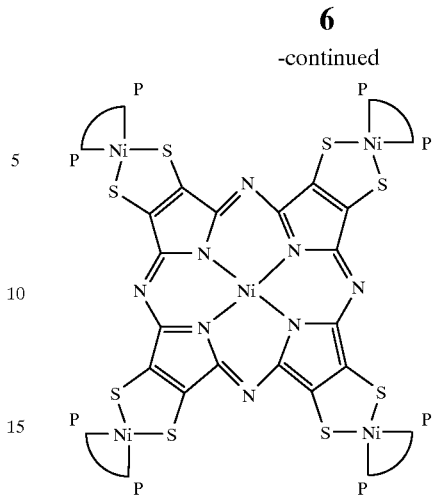

—P⌒P— is —P(C₆H₅)₂—CH₂CH₂—P(C₆H₅)₂—

Compound II is a porphyrazine compound bearing four dithiolene moieties (i.e., eight sulfide (S⁻) moieties), peripherally, at the β-pyrrole positions. The porphyrazineoctathiolate II, therefore, contains a porphyrazine ring system substituted with eight thiolate sulfur atoms at the β-pyrrole positions, which permits completing of four metal ions to the periphery of compound II in addition to one metal ion within the macrocyclic cavity of compound II. In other words, each of the four peripheral dithiolene moieties can be complexed with a metal ion. Compound II can behave either as a tridentate ligand at the periphery of the molecule (e.g., compound of structural formula III) or as a bidentate ligand at the periphery of the molecule (e.g., compound of structural formula IV).

Other publications relating to porphyrazine-2,3,7,8,12,13,17,18-octathiolate include:

C. T. Schramm et al., "Octakis(alkylthio)-tetraazaporphyrins", *Inorg. Chem.*, 19, pages 383–385 (1980);

C. S. Velázquez et al., "Metal-Encapsulated-Porphyrazines: Synthesis, X-Ray Crystal Structure and Spectroscopy of a Tetratin-star-Ni(porphyrazine)S₈ Complex", *J. Am. Chem. Soc.*, 112, pages 7408–7410 (1990); and C. S. Velázquez et al., "star-Porphyrazines: Synthetic, Structural, and Spectral Investigation of Complexes of the Polynucleating Porphyrazineoctothiolato Ligand", *J. Am. Chem. Soc.*, 114(19), pages 7416–7424 (1992).

SUMMARY OF THE INVENTION

The present invention is directed to porphyrazine compounds having one or more peripheral heteroatom moieties, either the same or different and in preselected number and geometric relationship, some of which can be capable of complexing with metal ions, thereby leading to the multimetallic complexes of the porphyrazine compounds having two to five metal ions, and to oligomers and polymers prepared from the multimetallic porphyrazine compounds. The porphyrazine compounds are substituted with a moiety at each of the eight peripheral β-pyrrole positions. To achieve peripheral metal binding, at least two, and up to eight, of the β-pyrrole positions are substituted with heteroatom moieties capable of complexing with a metal ion.

In particular, the present invention is directed to porphyrazine compounds having general structural formula V:

(III)

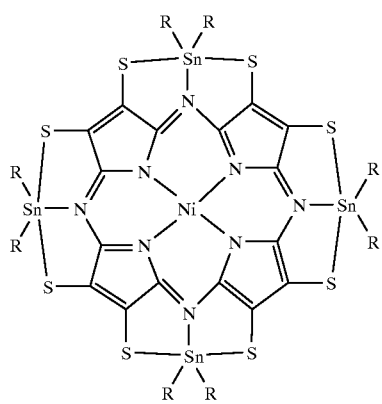

R is tertiary butyl (IV)

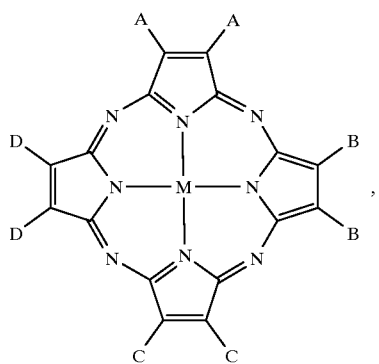

(V)

wherein M is 2H or an element capable of complexing with the pyrrole nitrogen atoms, and A, B, C, and D are independently selected from the group consisting of a thio moiety, an amino moiety, an oxo moiety, a phospho moiety, a seleno moiety, a telluro moiety and a hydrocarbon moiety, with the proviso that not all of A, B, C, and D are thio moieties and that not all of A, B, C, and D are hydrocarbon moieties.

One important aspect of the present invention is that the identity of moieties A, B, C, and D of compound V, and their geometric relationship, can be selected, along with element M, to provide desired optical, photophysical, dye or colorant properties, and/or physical properties (e.g., solubility), and/or chemical linking properties.

In accordance with an important aspect of the present invention, a porphyrazine compound V is interacted with a metal ion, wherein the metal ion complexes with the A, B, C, and D moieties capable of complexing with a metal ion, to provide a multimetallic porphyrazine compound complexing one to four metal ions to the periphery of the porphyrazine compound.

In one important embodiment of the present invention, moieties A, B, C, and D each are capable of complexing with a metal ion to provide a pentametallic porphyrazine compound having four metal ions complexed to the periphery of compound V and one element complexed within the macrocyclic cavity. In another important embodiment of the present invention, moieties A, B, C, and D of compound V are selected such that a dimetallic, trimetallic or tetrametallic porphyrazine compound is provided, wherein noncoordinating moieties are used to regulate solubility and/or other physical properties, or to provide a chemical link to a substrate or other molecule, such as for example, a polymer, like polystyrene, an inorganic solid, like hydroxyapatite or gold, glass, a dextran, a cyclodextran or an antibody.

Another aspect of the present invention is to provide oligomers and polymers prepared from the multimetallic porphyrazine compounds. The multimetallic porphyrazine compounds are linked to provide oligomers and polymers by edge-sharing the metal ions complexed at the periphery of the multimetallic porphyrazine compounds. The polymers can be linear (i.e., a ribbon polymer) or two-dimensional (i.e., a sheet polymer) depending upon the number of metal ions complexed to the periphery of the multimetallic porphyrazine compound.

A multimetallic porphyrazine compound having two metal ions peripherally complexed in a transconfiguration (i.e., metal ions complexed to moieties A and C in compound V) provide a ribbon polymer. A multimetallic compound having four metal ions peripherally complexed (i.e., metal ions complexed to moieties A, B, C, and D in compound V) provide a sheet polymer.

Another aspect of the present invention is to provide new magnet materials, conductors, imaging agents, and dyes based on the porphyrazines, the multimetallic complexes of the porphyrazines, and the oligomers and polymers prepared from the multimetallic porphyrazine compounds disclosed herein.

The above and other aspects and advantages of the present invention will become apparent from the following detailed description of the preferred embodiments.

DETAILED DESCRIPTION OF THE PREFERRED EMBODIMENTS

The novel porphyrazine compounds of the present invention have the general structural formula V:

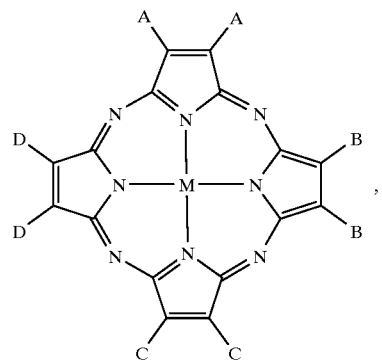

(V)

wherein M is 2H or an element capable of complexing with the pyrrole nitrogen atoms, and A, B, C, and D are independently selected from the group consisting of a thio moiety, an amino moiety, an oxo moiety, a phospho moiety, a seleno moiety, a telluro moiety and a hydrocarbon moiety, with the proviso that not all of A, B, C, and D are thio moieties and that not all of A, B, C, and D are hydrocarbon moieties.

The porphyrazine compounds V can be complexed with a variety of metal ions or metalloids to provide a multimetallic porphyrazine compound having an element M complexed within the central cavity of the porphyrazine compound, and having one to four metal ions $M^1$ complexed around the periphery of the porphyrazine compound.

The multimetallic porphyrazine compounds are formed by interacting a metal ion with a porphyrazine compound V. The metal ion complexes with moieties A, B, C, and D capable of complexing with a metal ion. In general, when an A, B, C, or D moiety is a sulfo moiety, an oxo moiety, an amino moiety, a phospho moiety, a seleno moiety or a telluro moiety, the metal ion is complexed to the peripheral β-pyrrole substituents of the porphyrazine compound. Hydrocarbon moieties do not complex with metal ions. Some heteroatom moieties also cannot complex with a metal ion and, like hydrocarbon moieties, are termed "noncoordinating" moieties.

Accordingly, the porphyrazine compounds V can have zero through four metal ions complexed to the periphery of the porphyrazine compound. Exemplary multimetallic porphyrazine compounds are illustrated in the following multimetallic porphyrazine compounds of general structural formulae VI–X:

(VI)
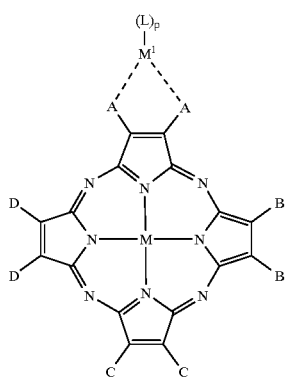

(IX)
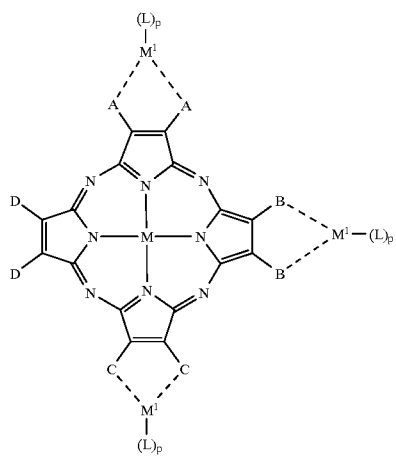

(VII)
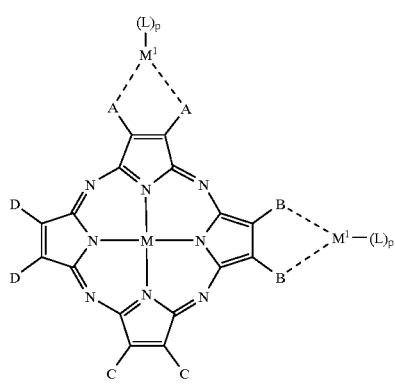

(X)
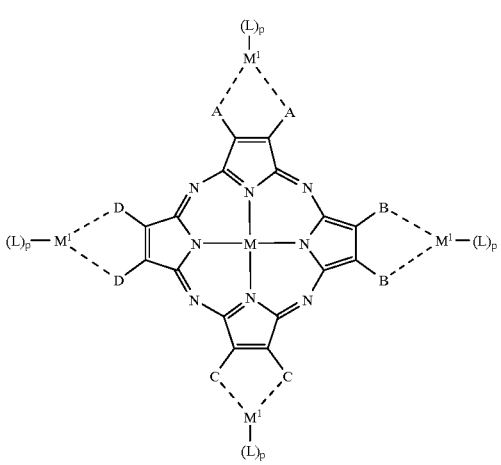

(VIII)
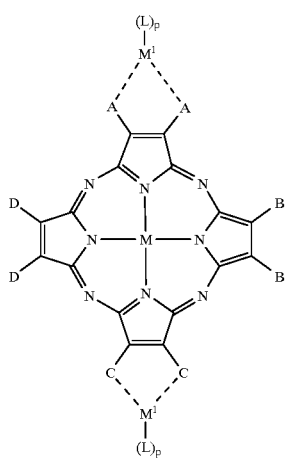

wherein M, A, B, C, and D have been defined above, $M^1$ is a metal ion, L is a ligand to complete the coordination shell of $M^1$, and p is an integer from 0 through 10.

Metal ion $M^1$ is any metal capable of complexing with the particular A, B, C, or D moieties present on the porphyrazine compound. Ligand L can be inorganic or organic in character, and often is the counterion of metal ion $M^1$. However, L can be any ligand capable of complexing with metal ion $M^1$. Ligands L are well known to persons skilled in the art.

Multimetallic porphyrazine compound VI is a bimetallic compound, wherein the A moieties are sulfo, oxo, amino, phospho, seleno or telluro moieties and the B, C and D moieties are noncoordinating moieties. Multimetallic porphyrazine compounds VII and VIII are trimetallic compounds having a cis- and trans- configuration, respectively. Multimetallic porphyrazine compounds IX and X are tetrametallic and pentametallic porphyrazine compounds, respectively.

For multimetallic compounds VI–X, moieties B, C and D that are not completed to a metal ion are noncoordinating moieties, either hydrocarbon or heteroatom, that can be selected to provide a desired physical property, such as solubility, or to provide a chemical link to a surface or to another molecule. Similarly, moieties A, B, C, and D of compounds VI–X that are complexed to a metal ion are sulfo-, oxo-, amino-, phosphor-, seleno- or telluro-moieties. For each compound VI–X, the central M element and the peripheral $M^1$ metal ions can be the same or different. Similarly, for compounds VII–X, the peripheral $M^1$ metal ions, and the ligands L, can be the same or different. When at least two metal ions are complexed to the periphery of a porphyrazine compound V (i.e., compounds VII–X), individual multimetallic porphyrazine compounds can be joined together to form an oligomer or a polymer.

The element M complexed within the macrocyclic cavity of porphyrazine compound V is 2H or any metalloid or metal ion capable of complexing with the pyrrole nitrogen atoms of the porphyrazine. Often, the metal ion initially is magnesium ion ($Mg^{+2}$) because the porphyrazine compounds V typically are prepared by the Linstead macrocyclization of 2,3-disubstituted maleonitriles in the presence of magnesium ion. However, after synthesis of a porphyrazine compound V, the magnesium ion can be replaced by two hydrogen atoms or by a different predetermined element M through transmetallation techniques well known in the art.

The element M of porphyrazine compounds V is not limited and can be two hydrogen atoms or any metal ion capable of being complexed by the macrocyclic cavity. Numerous different elements have been complexed within the macrocyclic cavity of porphyrazine. These elements include, but are not limited to, alkali metals, alkaline earth metals, transition metals of all three periods, lanthanides, actinides, aluminum, gallium, indium, thallium, germanium, tin, and lead. Nonlimiting examples of elements M include nickel, copper, two hydrogen atoms, magnesium, iron, aluminum, manganese, gadolinium, rhodium, indium, thallium, lanthanides, actinides, lutetium, gold, cobalt, titanium, lead, platinum, palladium, ruthenium, lithium, zinc, ytterbium, neodymium, chromium, technetium, silicon, germanium, tin, molybdenum, zirconium, tungsten, rhenium, iridium, uranium, thorium, gallium and vanadium. The identity of the particular element M depends upon the physical and chemical properties desired in porphyrazine compound V, such as magnetic moment, conductivity, or color.

It also should be understood that the element M of porphyrazine compounds V includes not only the metal ion, but any ligands for the metal ion needed to complete the valence shell of the element M. For example, if the metal ion is manganese (III), the element M contains a ligand, like chloride, to complete the valence shell of the manganese (III).

In accordance with an important feature of the present invention, a preferred element M is a transition metal or a rare earth metal. To achieve the full advantage of the present invention, the element M comprises two hydrogen atoms, nickel, copper, magnesium, iron, ruthenium, manganese, cobalt, palladium, platinum, gadolinium, zinc, aluminum, vanadium, or silicon.

The moieties A, B, C, and D of a porphyrazine compound V are independently selected from the group consisting of a thio moiety, an amino moiety, an oxo moiety, a phospho moiety, a seleno moiety, a telluro moiety, and a hydrocarbon moiety. A hydrocarbon moiety is defined herein as including hydrogen. In accordance with an important feature of the present invention, the moieties A, B, C, and D are not all thio moieties, and the moieties A, B, C, and D are not all hydrocarbon moieties. Otherwise, by a judicious selection of starting materials and ratio of starting materials, any combination of different A, B, C, and D moieties on a porphyrazine compound V can be achieved. In addition, as demonstrated hereafter, the various porphyrazines and metallated porphyrazines VI–X can be isolated and purified based on solubility differences and using chromatographic techniques.

In accordance with an important feature of the present invention, all of the A, B, C, and D moieties cannot be hydrocarbon moieties. At least one of the A, B, C, and D moieties must be a heteroatom moiety, and one or more can be capable of complexing with an $M^1$ metal ion at the periphery of porphyrazine compound V. The ability to complex at least one $M^1$ metal ion at the periphery of the porphyrazine compound permits preparation of multimetallic porphyrazine compounds, and oligomers and polymers are prepared therefrom. Porphyrazine compounds having a varying number of A, B, C, and D moieties were prepared, including compounds having unexpected optical and/or solubility properties, as well as compounds capable of complexing with metal ions, which were then converted into multimetallic porphyrazine compounds VI–X having $M^1$ metal ions complexed with the peripheral heteroatoms, as well as an element M complexed within the central cavity of porphyrazine V.

If the A, B, C, and/or D moiety is a thio moiety, the thio moiety can be, for example, sulfo ($S^-$), sulfhydryl (—SH) or alkylthio (—SR), wherein R is an alkyl group having one to 10 carbon atoms, a polyethylene oxide chain having one to twenty ethylene oxide units, phenyl, benzyl or allyl, or R is a benzyl blocking group, like p-carboxybutyl benzyl (Bnbe), for example.

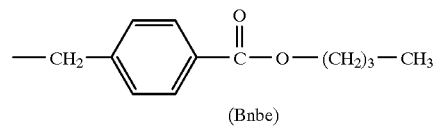

(Bnbe)

In addition, the A moieties, B moieties, C moieties or D moieties can be taken together to form a ring containing at least two sulfur atoms. In this case, for example, the thio moiety can have the dithiolate structure —S—$(CH_2$—S$)_q$—,
—S—$(CH_2CH_2$—S$)_q$— or
—S—$(CH_2CH_2CH_2$—S$)_q$—, wherein q is an integer from 2 through 6, or the thio moiety can be trithiocarbonate.

The thio moieties also can be —SSi$(R_7)_3$, wherein the $R_7$ groups are selected independently from an alkyl group having one to 16 carbon atoms and phenyl; —SCH$_2$(CH$_2$)$_c$O(CH$_2$(CH$_2$)$_c$O)$_d$R$_9$ or —SCH$_2$(CH$_2$)$_c$S(CH$_2$—(CH$_2$)$_c$O)$_d$R$_9$, wherein c is one or two, d is an integer from one to five, and R$_9$ is hydrogen or an alkyl group having one to 16 carbon atoms; —SCH$_2$(CH$_2$)$_c$E(CH$_2$(CH$_2$)$_c$F)—$_d$R$_9$, wherein E and F are independently selected from the group consisting of selenium, tellurium, alkyl-amino (wherein the alkyl group has one to 16 carbon atoms), alkyl (wherein the alkyl group has two to ten carbon atoms), p-toluenesulfonamide, 2-pyridylmethyl, $COCH_2COR_9$, $CH_2COCH_2COR_9$, $CH_2CO_2H$, and acetamide, and c, d, and $R_9$ are defined above.

An exemplary, but nonlimiting, porphyrazine compound V wherein the A moieties are sulfo moieties taken together as trithiocarbonate and the B moieties are sulfo moieties taken together as a dithiolate moiety is illustrated in the porphyrazine compound of structural formula XI.

(XI)

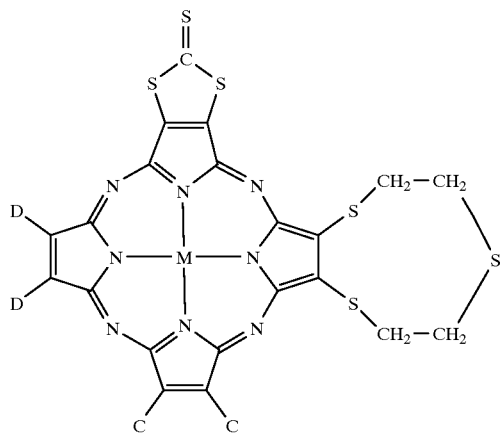

If the A, B, C, and/or D moiety is an amino moiety, the amino moiety has the structure

wherein $R_1$ and $R_2$ can be same or different and are selected from the group consisting of hydrogen, an alkyl group having one to 16 carbon atoms, 2-pyridylmethyl, benzyl, allyl, $-CH_2CO_2H$, $-COCH_2OR_{15}$, and $-CH_2CO-CH_2COR_{15}$, wherein $R_{15}$ is an alkyl group having one to 16 carbon atoms. The A, B, C, and D moieties also can be taken together to form a ring containing at least two nitrogen atoms, such as, but not limited to $-NR_{16}-(CH_2)_q-NR_{16}-$, $-NR_{16}-(CH_2-NR_{16})_q-CH_2NR_{16}-$, $-NR_{16}-(CH_2CH_2CH_2-NR_{16})_qCH_2CH_2CH_2NR_{16}-$, and/or $-NR_{16}-(CH_2CH_2NR_{16})_2CH_2CH_2NR_{16}-$, wherein q is an integer from 2 through 6, and $R_{16}$ is hydrogen, an alkyl group having one to ten carbon atoms, 2-pyridylmethyl, benzyl, allyl, $-CH_2CO_2H$, $-COCH_2OR_{10}$, and $-CH_2COCH_2COR_{10}$, wherein $R_{10}$ if an alkyl group having one to twelve carbon atoms.

An exemplary, but nonlimiting, porphyrazine compound V wherein the A moieties are amino moieties and the C moieties are carboxylic acid-substituted amino-moieties is illustrated in the porphyrazine compound of structural formula XII.

(XII)

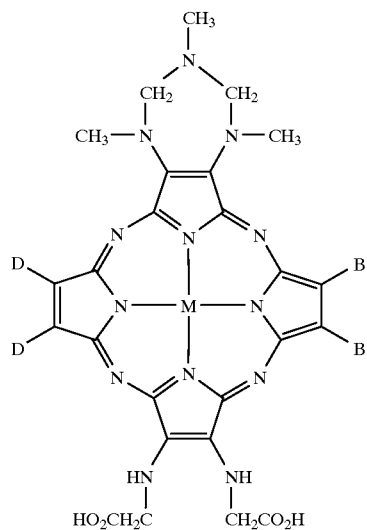

An exemplary porphyrazine compound V having A and C moieties being amino moieties and B and D moieties being trithiocarbonate is illustrated hereafter as compound having structural formula L. Compound L illustrates the mixing of different types of heteroatoms and heteroatom moieties in a compound V.

If the A, B, C, and/or D moiety is an oxo moiety, the oxo moiety can be oxo ($O^-$), hydroxyl ($-OH$), alkoxy ($-OR_{17}$), acyloxy ($-OCOR_{17}$), or silyloxy ($-OSi(R_{17})_3$) wherein $R_{17}$ is an alkyl group having one to 12 carbon atoms or $R_{17}$ is a benzyl group or a phenyl group, like

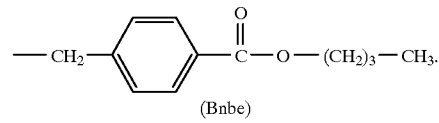

(Bnbe)

In addition, the A, B, C, or D moieties can be taken together to form a ring containing at least two oxygen atoms, or at least one oxygen atom and either one nitrogen, sulfur, tellurium or selenium atom. In this case, the oxo moiety for example can have the structure

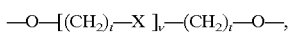

wherein X is sulfur, oxygen, $-PR_{11}$, selenium, tellurium, or $-NR_{11}$, wherein $R_{11}$ is selected from the group consisting of hydrogen, an alkyl group having one to six carbon atoms, 2-pyridylmethyl, benzyl, allyl, $-CH_2CO_2H$, $-COCH_2OR_{10}$, and $-CH_2OCCH_2COR_{10}$, wherein $R_{10}$ is an alkyl group having one to twelve carbon atoms, v is an integer 1 through 6, and t is an integer 1 through 3. The oxo moiety also can be carbonate.

An exemplary, but nonlimiting, porphyrazine compound V, wherein the B moieties are benzyl blocking group alkoxy moieties (i.e., Bnbe) and the D moieties are taken together as a dioxo-moiety is illustrated in the porphyrazine compound of structural formula XIII.

(XIII)

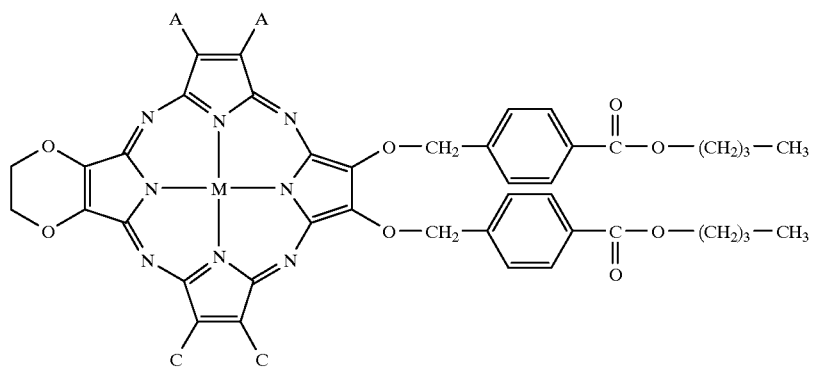

In addition, the oxo moieties can be a part of a crown ether, wherein the oxo moieties form a ring and have the structure (XIV)

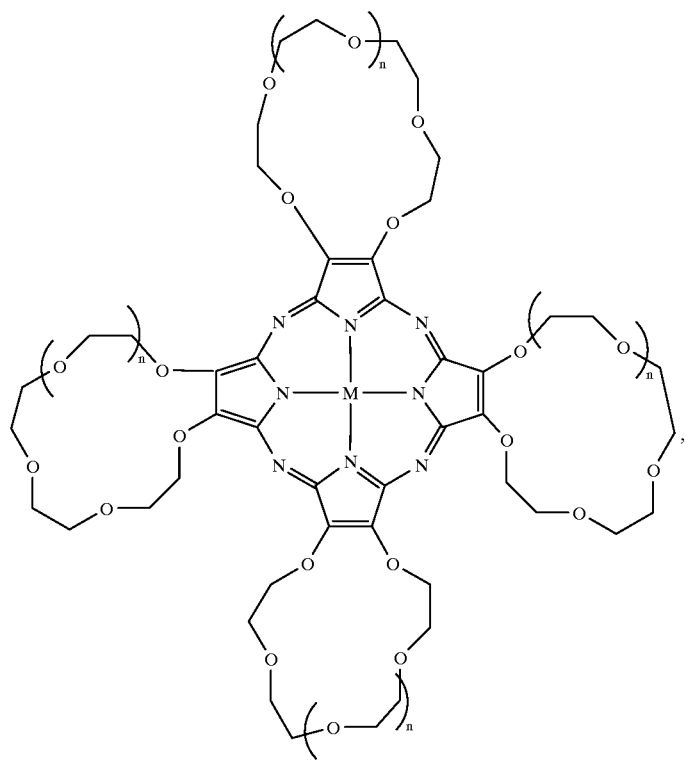

$$-O-\!\!\!+\!\!(CH_2)_2-O-\!\!\!\!\frac{}{q}\,CH_2CH_2-O-,$$

wherein q is an integer from 2 through 6. The oxygen atoms can be substituted, individually or collectively, with nitrogen, sulfur, phosphorus, tellerium or selenium in the crown ether.

An exemplary, but nonlimiting, porphyrazine compound V wherein the oxo moieties are part of a crown ether is illustrated in the porphyrazine compound of structural formula XIV, wherein the A, B, C, and D moieties each are taken together as a portion of a crown ether.

wherein n is 1 or 2.

The oxo moieties also can be hydroxyl moieties reacted with diol-protecting groups to form a ring having at least two oxygen atoms. Exemplary and nonlimiting porphyrazine compounds V, wherein the B moieties are hydroxyl (—OH) moieties modified with a diol-protecting group, are illustrated below:

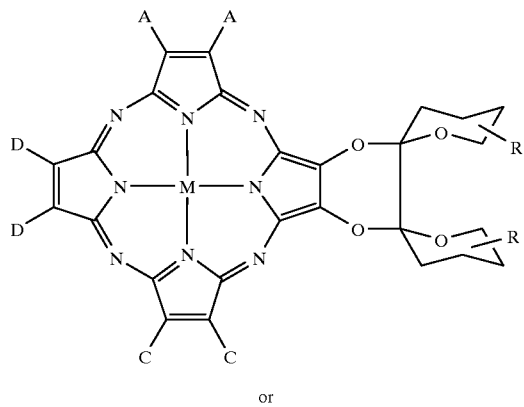

or

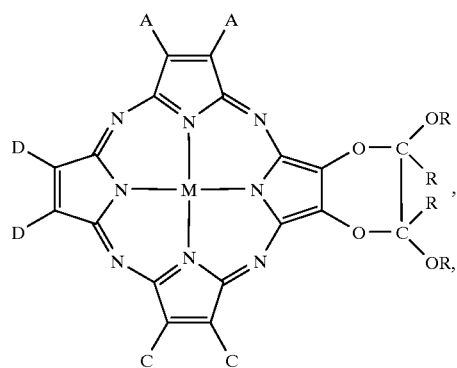

wherein R has been defined previously. The A, C, and/or D moieties can be similar oxo moieties.

Similarly, a thio moiety or an amino moiety can be a portion of a crown ether, as illustrated in the porphyrazine compound of structural formula XV, wherein the B moieties are thio moieties and the D moieties are amino moieties, all of which are a portion of a crown ether.

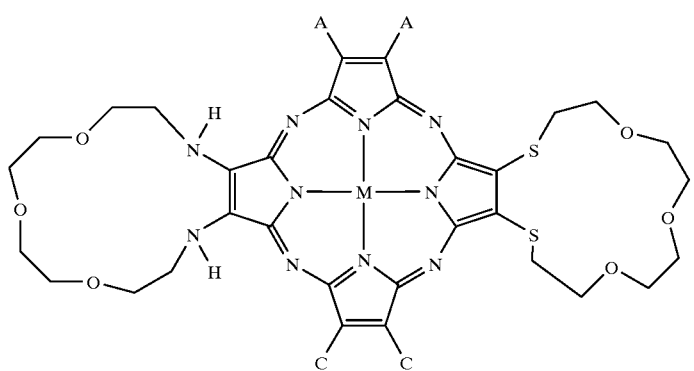

If the A, B, C, or D moiety is a phospho moiety, the phospho moiety can be alkylphosphino (—$PR_3R_4$), wherein $R_3$ and $R_4$ can be the same or different and are alkyl groups having one to 12 carbon atoms, benzyl, phenyl, polyethyleneoxy or polyphenyl ether, or a phosphonite ester (P(OR$_5$)). The phospho A, B, C, or D moieties also can be taken together to form a ring. In this case the phospho moiety has the structure

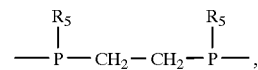

wherein $R_5$ is an alkyl group having 1 to 12 carbon atoms, phenyl, or the phospho moiety has the structure

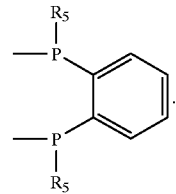

An exemplary, but nonlimiting, porphyrazine compound V wherein the A moieties are phosphino and the B moieties are taken together as 1,2-diphosphinophenyl is illustrated in the porphyrazine compound of structural formula XVI.

(XVI)

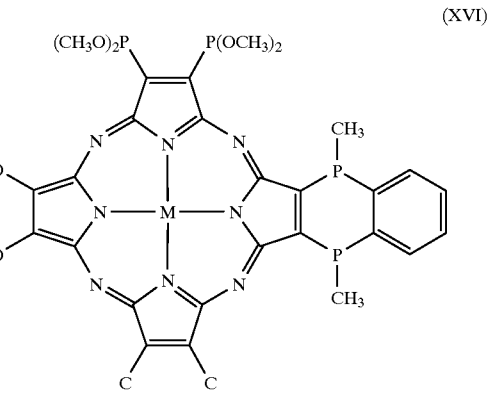

(XV)

If the A, B, C, or D moiety is a seleno or telluro moiety, the moiety can be seleno (—SeH or —Se$^-$), telluro (—TeH or Te$^-$), alkylseleno or alkyltelluro (—Se(Te)R$_6$), wherein $R_6$ is an alkyl group having one to 12 carbon atoms, allyl, phenyl or benzyl.

Specific seleno- and telluro-moieties include, but are not limited to:

—Se(Te)H;

—Se(Te)M$^2$, wherein M$^2$ is an alkali metal ion or an alkaline earth metal ion;

—Se(Te)Si(R$_7$)$_3$, wherein the R$_7$ groups are selected independently from an alkyl group having one to 12 carbon atoms and phenyl;

—Se(Te) CH$_2$CH=CH$_2$;

—Se(Te)Ph, wherein Ph is phenyl;

—Se(Te)Bn, wherein Bn is benzyl;

—Se(Te)CH$_2$C$_6$H$_4$—4—CO$_2$R$_8$, R$_8$ is an alkyl group having one to six carbon atoms or phenyl;

—Se(Te)CH2(CH$_2$)$_c$O(CH$_2$(CH$_2$)$_c$O)$_d$R$_9$ or —Se(Te)CH$_2$(CH$_2$)$_c$S(CH$_2$(CH$_2$)$_c$O)$_d$R$_9$, wherein c is one or two, d is an integer from one to five, and R$_9$ is hydrogen or an alkyl group having one to 16 carbon atoms; and —Se(Te)CH$_2$(CH$_2$)$_c$E(CH$_2$(CH$_2$)$_c$F)$_d$R$_9$, wherein E and F are independently selected from the group consisting of selenium, tellurium, alkylamino (wherein the alkyl group has one to five carbon atoms), alkyl (wherein the alkyl group has two to ten carbon atoms), p-toluenesulfonamide, acetamide, 2-pyridylmethyl, —COCH$_2$COR$_9$, —CH$_2$COCH$_2$COR$_9$, and c, d, and R$_9$ are defined above.

If the A, B, C, or D moiety is a hydrocarbon moiety, the hydrocarbon moiety can be hydrogen, an alkyl group having one to four carbon atoms, phenyl, alkylphenyl or alkoxyphenyl wherein the alkyl or alkoxy group has one to 12 carbon atoms, or polyethyleneoxyphenyl. The hydrocarbon A, B, C, or D moieties also can be taken together as part of a ring system, such as benzo.

The hydrocarbon moiety also can be a substituted or unsubstituted alkene or alkyne. In one embodiment, the hydrocarbon moiety is a strained alkene, for example:

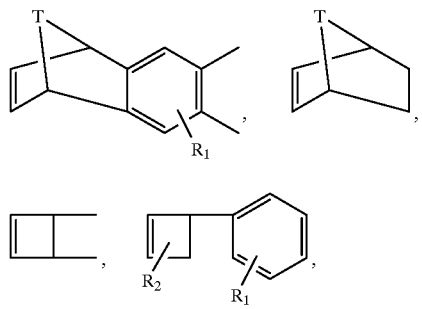

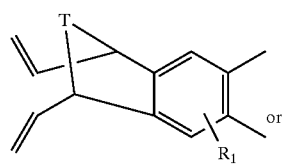

wherein R$_1$ and R$_2$ have been defined previously, and T is selected from the group consisting of O, S, NR$_{26}$, and C(R$_{26}$)$_2$, wherein R$_{26}$ is selected, independently, from the group consisting of hydrogen, C$_1$–C$_4$ alkyl, C$_1$–C$_4$ alkoxy, and benzyl, or a diene, for example:

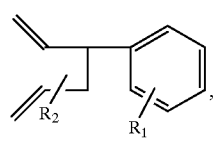

-continued wherein T, R$_1$, and R$_2$ have been defined previously.

Unsubstituted strained alkenes and dienes are exemplified by:

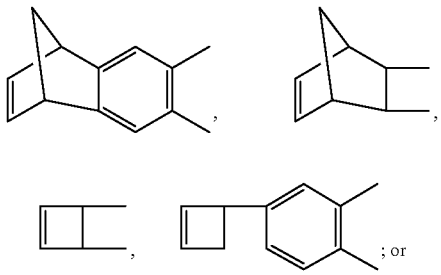

a diene like

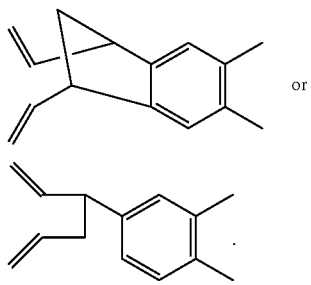

The hydrocarbon moiety also can be an oligomer or polymer derived from such strained alkenes and dienes. In addition, a porphyrazine oligomer or polymer can be formed by polymerizing the strained alkene or diene hydrocarbon moieties, thereby linking individual porphyrazine compounds.

The moieties A, B, C an D can be selected to provide a porphyrazine compound V capable of complexing one to four metal ions around the periphery of the compound, as illustrated in compounds VI–X. Moieties capable of complexing metal ions to the periphery of the compound have oxo, amino, phospho, seleno and/or telluro moieties. For example, if all eight A, B, C, and D moieties are amino moieties, such as in the compound of structural formula XVII, four metal ions M$_1$ can be complexed around the periphery of the compound, in addition to the element M complexed in the macrocyclic cavity.

(XVII)

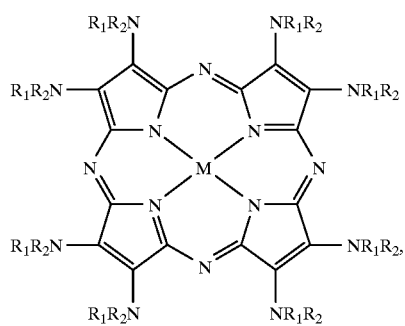

wherein $R_1$ and $R_2$ have been defined previously.

Similarly, if all eight A, B, C, D moieties are oxo, such as in the crown ether-encircled porphyrazine compound illustrated in general structural formula XVIII, four metal ions ($M^1$) can be complexed within the crown ether moieties and around the periphery of the porphyrazine compound, in addition to the element complexed in the macrocyclic cavity.

(XVIII)

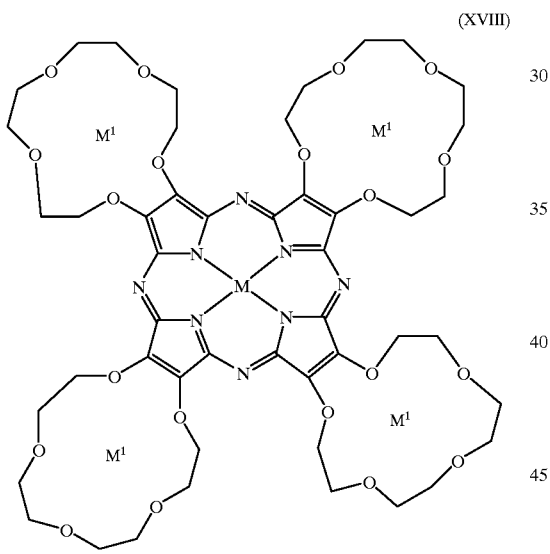

If less than all eight A, B, C, and D moieties are capable of complexing with a metal ion, then the porphyrazine compound V complexes one to three metal ions to the periphery of the compound to form a multimetallic porphyrazine compound. For example, if A is a thio moiety (e.g., —SR) and B, C and D are hydrocarbon moieties (e.g., benzo), the following porphyrazine compound XIX is provided. Porphyrazine compound XIX can be complexed with one metal ion ($M^1$)

(XIX)

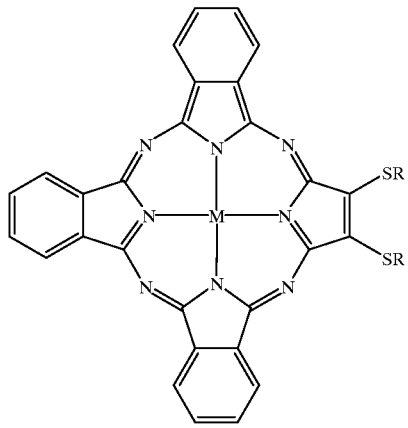

at the periphery of the compound to provide the multimetallic porphyrazine compound XX, wherein L is a ligand, or ligands, which fills the coordination sphere of the metal ion ($M^1$).

(XX)

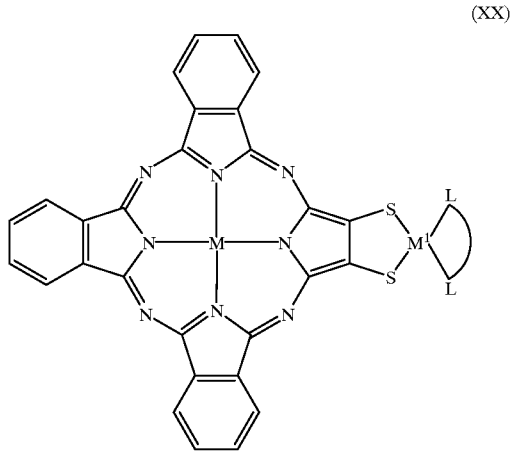

For example, A, B and C can be a crown ether and D can be a moiety (e.g., such as an alkyl group R) selected to increase the solubility of the compound in common solvents, or to provide a chemical link to a surface, like to a gold surface, or to another molecule, such as an antibody, polystyrene or a dextran. An exemplary compound has the structural formula XXa.

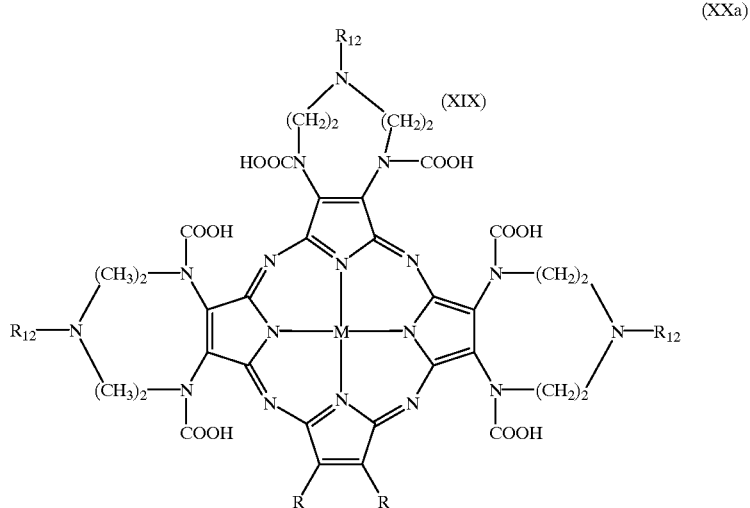

(XXa)

wherein $R_{12}$ is an alkyl group having one to 10 carbon atoms or $-CO_2H$, and each carboxylic acid-functionalized aza-crown ether is further complexed with a predetermined $M^1$ metal ion to provide an MRI contrast agent or a radiopharmaceutical.

The multimetallic porphyrazine compounds VI–X derived from porphyrazine compounds V are used as monomers to form polymacrocyclic compounds of predetermined oligomeric association. Such a polymacrocyclic oligomer is exemplified by the compound of structural formula XXI, which contains three multimetallic porphyrazine compounds united by edge-sharing peripherally complexed platinum ions. The compound of structural formula XXI is a combination of: (a) a trimetallic porphyrazine compound capable of complexing with two metal ions ($M^1$) at the periphery of the compound (i.e., the central porphyrazine) and (b) two dimetallic porphyrazine compounds capable of complexing with one metal ion ($M^1$) at the periphery of the compound (i.e., the terminal porphyrazines). The compound of structural formula XXI also illustrates that the moieties A, B, C, and D and element M can be independently selected, and that thio, amino and hydrocarbon moieties are present in the porphyrazine oligomer.

The present porphyrazine compounds V can be used to prepare a wide variety of multimetallic porphyrazine compounds having different internal (M) element and peripheral ($M^1$) metal ions. The identity of the peripherally complexed metal ion is not limited, but is determined by the identity of the A, B, C, and D moieties present on the porphyrazine. By a judicious selection of A, B, C, and D moieties, essentially any metal ion can be complexed to the periphery of the porphyrazine. Accordingly, the multimetallic porphyrazine compounds have a wide range of physical and chemical properties, and particular multimetallic porphyrazine compounds can be designed for a particular application by a proper selection of A, B, C, and D moieties and a proper selection of the metals complexed in the core of the compound (M) and at the periphery of the compound ($M^1$).

To illustrate the porphyrazine compounds of the present invention, the following are nonlimiting examples of the present porphyrazine compounds and multimetallic porphyrazine compounds prepared therefrom.

EXAMPLE 1

Preparation of the Norphthalocyanine Dithiolate (Compound of Structural Formula XIX)

Compound XIX was prepared selectively by the mixed condensation of excess 1,2-dicyanobenzene 1 with the dithi-

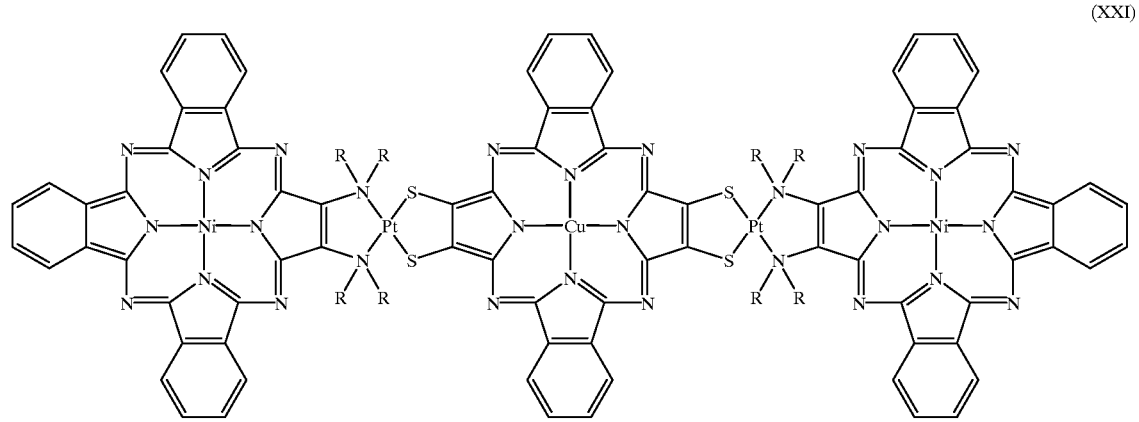

(XXI)

omaleonitrile derivative 2, as set forth in the following reaction scheme, using Mg(II) as a template. Compound XIX was prepared using the Linstead macrocyclization procedure in a crossover macrocyclization. The reaction yielded a soluble, thio-protected Mg(norphthalocyanine) derivative (i.e., compound XIX wherein M is Mg and R is Bnbe) in 16–18% yield. The compound of structural formula XIX was soluble in the butanol (BuOH) solvent and was easily separated from the insoluble reaction by-products, such as magnesium phthalocyanine.

The magnesium-complexed porphyrazine compound XIX then was demetalated with trifluoroacetic acid, by procedures well known in the art, to provide compound XIX wherein M is 2H and R is Bnbe. This compound then was remetalated with a metal acetate (i.e., M(OAc)$_2$, wherein M is Ni(II) or Cu(II)) to provide essentially quantitative yields of compounds XIX wherein M is nickel(II) or copper(II) and R is Bnbe. Each of the porphyrazine compounds XIX wherein M is 2H, Ni(II) or Cu(II) was subjected to reductive debenzylation using sodium in liquid ammonia (Na/NH$_3$) to produce the norphthalocyanine dithiolates XIX wherein M is 2H, Ni(II) or Cu(II) and R is H. Each of these porphyrazine compounds was capped in situ with [1,1'-bis(diphenylphosphino)ferrocene] palladium(II), (i.e., (P-P)PdCl$_2$), to give dimetallic porphyrazine compounds of structural formula XX in 30% yield.

The resulting multimetallic compounds had a central metal ion M of 2H, Ni (II) or Cu(II). Reaction with the palladium(II) compound provided a multimetallic compound wherein the $M^1$ of compound XX is Pd(II) and L is a diphosphine ligand.

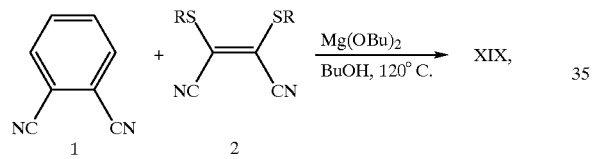

wherein R =

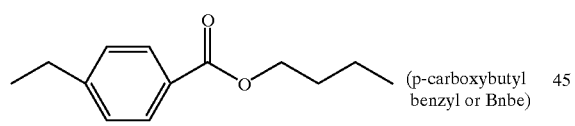

(p-carboxybutyl benzyl or Bnbe)

and Bu (n-butyl)

The multimetallic porphyrazine compounds XX wherein M is 2H, Ni(II) or Cu(II) were characterized by X-ray crystallography. It was observed that the porphyrazine ring was essentially planar. X-ray crystallography also demonstrated asymmetry at the periphery of the compound.

The four-coordinate palladium(II) ion was complexed by the two peripheral thio moieties and by the two phosphorus atoms of the diphosphorus ligand. The dithiolene unit of the compound adjusts itself in order to chelate the palladium ion by a swing of the C$_\beta$-S bond.

Compound XIX is an example of a porphyrazine compound having one metal ion complexing site present on the periphery of the compound. Compound XIX, therefore, is capable of coordinating with a single exocyclic $M^1$ metal ion in addition to an M metal ion within the central macrocyclic cavity.

The synthesis and characterization of compounds XIX and XX is set forth in T. F. Baumann et al., "Solitaire Porphyrazines: X-ray Crystal Structure and Spectroscopy of [1,1'-Bis (diphenylphosphino)-ferrocene]-[(norphthalocyanine)dithiolate] palladium(II)," J. Am. Chem. Soc., 116, pages 2639–2640 (1994), incorporated herein by reference.

Other porphyrazine compounds V having thio or hydrocarbon A, B, C, and D moieties are illustrated in compounds XXII and XXIII, wherein M is 2H, Ni(II) or Cu(II).

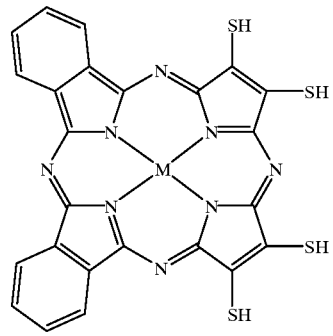

(XXII)

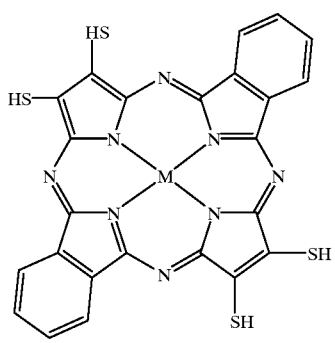

(XXIII)

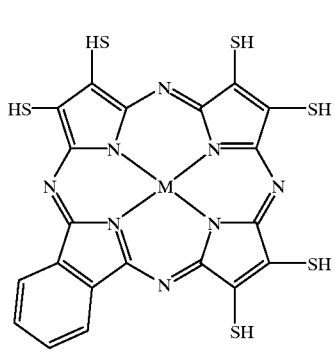

(XXIIIa)

Unlike compound XIX which is produced selectively, compounds XXII, XXIII and XXIIIa were produced simultaneously during the macrocyclization reaction. In addition, other porphyrazine compounds also were produced simultaneously as by-products because six compounds can be formed by macrocyclizing a 1:1 mole ratio of two different maleonitrile compounds. However, the six possible reaction products can be readily separated chromatographically based on disparate polarities between the products.

Compounds XXII and XXIII, wherein M is Ni(II), were separated from reaction by-products and from each other, based on polarity differences between the compounds. In particular, compounds XXII and XXIII could be separated because of the difference in polarity between the Bnbe groups protecting the sulfo moieties and the benzo groups. After separation, the cis and trans compounds were debenzylated to provide compounds XXII and XXIII, respectively. The thio moieties then were metallated with $PtCl_2(PEt_3)_2$ (Et is ethyl) to provide crystallographically characterized, analytically pure, multimetallic compounds that are stable and soluble in organic solvents.

In analogous fashion, compounds of structural formula XXIIIb, wherein M is zinc, aluminum or manganese, can be prepared and separated from reaction by products and undesirable isomers because of polarity differences, and thereby isolate compounds having optical properties useful for optical imaging and photodynamic therapy.

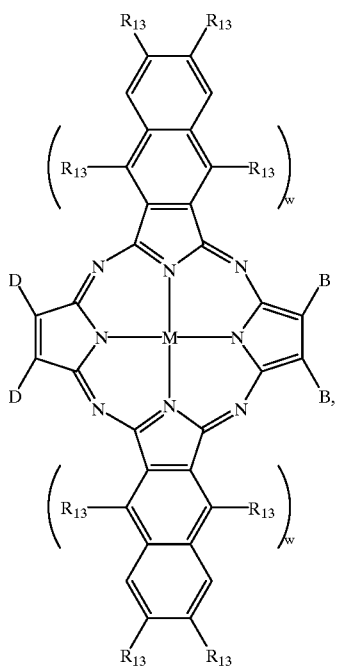

(XXIIIb)

wherein w is an integer 0 through 3, $R_{13}$, independently, is hydrogen, an alkyl group or an alkoxy group having one to ten carbon atoms, polyethyleneoxy or polyphenoxy. M, B, and D have been defined previously.

EXAMPLE 2

Preparation of Porphyrazinoctamine Compounds (Compounds of Structural Formula XVII)

Commercially available diaminomaleonitrile 1 first was converted into a N,N,N',N'-tetraalkyl derivative 2 by procedures known and published in the art using dimethyl sulfate ($Me_2SO_4$) and sodium hydride (NaH) in 1,2-dimethoxyethane (DME). Five tetraalkyl derivatives 2 were prepared: (a) tetramethyl (53% yield), (b) tetrabenzyl (53%), (c) N,N'-dimethyl N,N'-dibenzyl (64%), (d) N,N'-dimethyl N,N'-diallyl (80%) and (e) N,N'-di-2-pyridylmethyl N,N'-dimethyl (51%). The di-2-pyridylmethyl dimethyl derivative was prepared by sequential double reductive alkylation of diaminomaleonitrile 2 using pyridine-2-carboxaldehyde and methylation.

Each of the five tetraalkyl dinitriles 2 was readily cyclized using the Linstead macrocyclization technique with magnesium propoxide as a template. The synthetic route is illustrated in the following scheme.

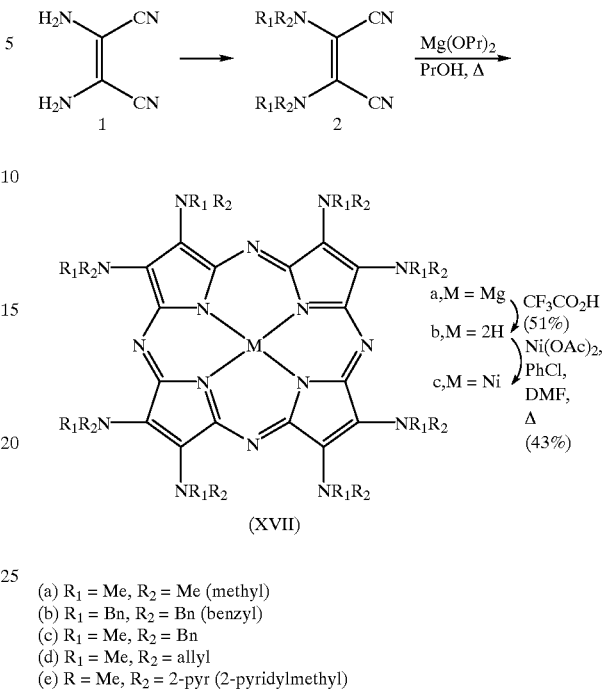

(a) $R_1$ = Me, $R_2$ = Me (methyl)
(b) $R_1$ = Bn, $R_2$ = Bn (benzyl)
(c) $R_1$ = Me, $R_2$ = Bn
(d) $R_1$ = Me, $R_2$ = allyl
(e) R = Me, $R_2$ = 2-pyr (2-pyridylmethyl)

Heating a propanol (PrOH) solution of a dinitrile 2 under reflux with magnesium propoxide ($Mg(OPr)_2$) yielded the porphyrazines of structural formula XVII wherein $M^1$ is magnesium. Each of the five magnesium porphyrazines was isolated and purified by chromatography on neutral alumina. Each of the five magnesium porphyrazine compounds was a blue-black solid with purple reflections.

Each of the five magnesium porphyrazine compounds XVII was demetallated with trifluoroacetic acid ($CF_3CO_2H$) to provide a porphyrazine compound XVII wherein M is 2H. Subsequent reaction with nickel(II) acetate ($Ni(OAc)_2$) resulted in selective metallation within the macrocyclic cavity to provide the nickel(II) porphyrazine compounds (i.e., compound XVII wherein M is Ni(II)). Spectroscopic data, including infrared, ultraviolet, nuclear magnetic resonance and mass spectroscopy, confirmed the preparation of the porphyrazine compounds XVII. Single crystal X-ray determinations also were performed on the magnesium porphyrazine compound XVII having tetrabenzyl substituents, and on the nickel porphyrazine compound XVII having two benzyl and two allyl substituents. The two compounds were recrystallized from chlorobenzenemethanol and ethyl acetate-hexane, respectively, and the X-ray determinations confirmed the structures of the porphyrazine compounds. The porphyrazine compounds XVII are capable of providing a pentametallic porphyrazine compound because of the presence of eight amino moieties.

The synthesis and characterization of porphyrazine compounds XVII is set forth in N.S. Mani et al., "Synthesis and Characterisation of Porphyrazineoctamine Derivatives: X-Ray Crystallographic Studies of [2,3,7,8,12,13,17,18-Octakis (dibenzyl-amino)porphyrazinato]magnesium (II) and {2,3,7,8,12,13,17,18-Octakis [allyl (benzyl) amino]-porphyrazinato}nickel (II)", *J. Chem. Soc., Chem. Comm.*, pages 2095–2096 (1994), incorporated herein by reference.

The following synthetic scheme illustrates the preparation of porphyrazinodiamine compound XXIV, which is capable of providing a dimetallic porphyrazine compound. The porphyrazine compound XXIV is prepared using the crossover Linstead macrocyclization technique.

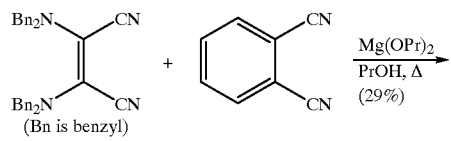
(Bn is benzyl)

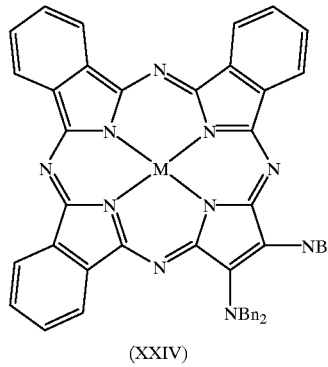
(XXIV)

Other porphyrazine compounds V wherein the A, B, C, and D moieties are amino or hydrocarbon moieties also can be prepared. For example, the porphyrazinoctamine compound XVII, wherein $R_1$ is methyl and $R_2$ is —$CH_2CO_2H$ can be prepared from diaminomaleonitrile, t-butyl glyoxalate (t-Bu—$O_2$CCHO) and dimethyl sulfate. In addition, compound XVII wherein $R_1$ and $R_2$ are H can be prepared from compound XVII wherein $R_1$ and $R_2$ are benzyl by hydrogenolysis or dissolving metal reduction. The resulting compound XVII wherein $R_1$ and $R_2$ are H then can be reacted with formylacetone to provide compound XVII wherein $R_1$ is H and $R_2$ is —CH=CHCOCH$_3$.

The porphyrazine compound XVII wherein $R_1$ is H and $R_2$ is 2-pyridylmethyl can be prepared by a Linstead macrocyclization of maleonitrile XXV, a compound which has been synthesized and characterized.

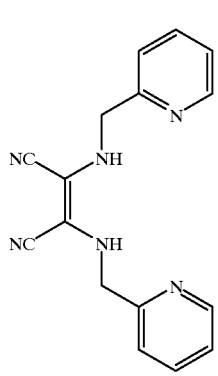
(XXV)

In addition, the porphyrazine compound XXVI, wherein Pyr is 2-pyridylmethyl and n is 1 or 2, can be prepared from diamine XXV by reaction with $I(CH_2CH_2O)_aCH_2CH_2I$, wherein a is 3 or 4, and Linstead macrocyclization.

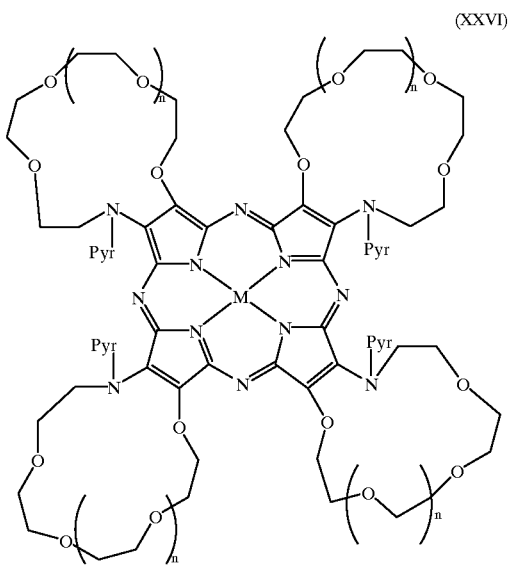
(XXVI)

Similar to porphyrazine XXVI, a porphyrazine V, having thio or amino moieties incorporated in a crown ether can be prepared by Linstead macrocyclization of the precursor hetero-functionalized maleonitrile class of compounds, exemplified by compound XXVII, wherein n is 1 or 2.

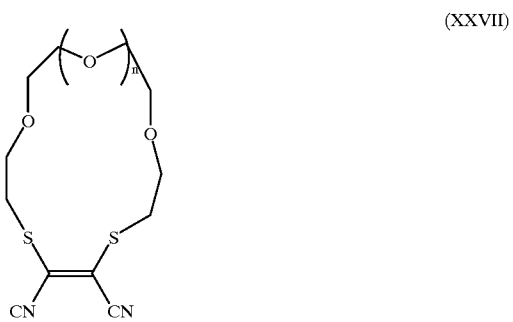
(XXVII)

EXAMPLE 3

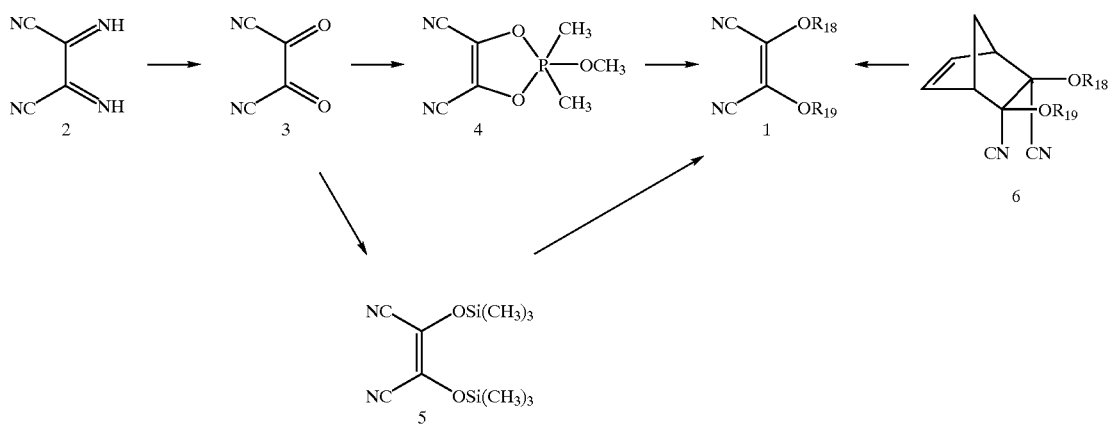

The Linstead macrocyclization of dinitrile 1 and subsequent deprotection of the oxygen atoms proceeds in a manner similar to the sulfur analog of Example 1. Dinitrile 1 is prepared by selectively hydrolyzing diiminosuccinonitrile 2 to provide oxalyl cyanide 3, as reported in the literature. Oxalyl cyanide 3 is reduced by a cis-directing reductant, such as trialkyl phosphite, like trimethyl phosphate, hexamethyldisilane or a zerovalent metal carbonyl. The resulting products, such as compounds 4 and 5, are dioxolene equivalents which can be hydrolyzed and alkylated to provide dinitrile 1, wherein $R_{18}$ is hydrogen, an alkyl group having one to four carbon atoms or benzyl, and $R_{19}$ is an alkyl group having one to 12 carbon atoms or benzyl, or $R_{18}$ and $R_{19}$ are taken together to form an aliphatic ring, i.e., a crown dicyanoethylene. Dinitrile 1 also can be prepared from dinitrile 6 by a retro Diels-Alder reaction.

Dinitrile 1 then is macrocyclized by the Linstead macrocyclization procedure in the manner described in Examples 1 and 2 to provide a porphyrazine compound V, wherein the A, B, C, and D moieties are all oxo moieties, or are a combination of oxo and hydrocarbon moieties.

EXAMPLE 4

Macrocyclization of diimine 1 proceeds in a manner similar to the macrocyclizations set forth in Examples 1–3. Diimine 1, wherein $R_7$ is an alkyl group having one to 16 carbon atoms, phenyl or substituted phenyl, is prepared by reacting dichloride 2 with the lithium phosphide, $LiP(R_7)_2$, to provide diphosphine 3. Ammonolysis of diphosphine 3 provides diimine 1, which is stable and can be macrocyclized by the Linstead technique in the manner described in Examples 1–3 to provide a porphyrazine compound V having phospho moieties.

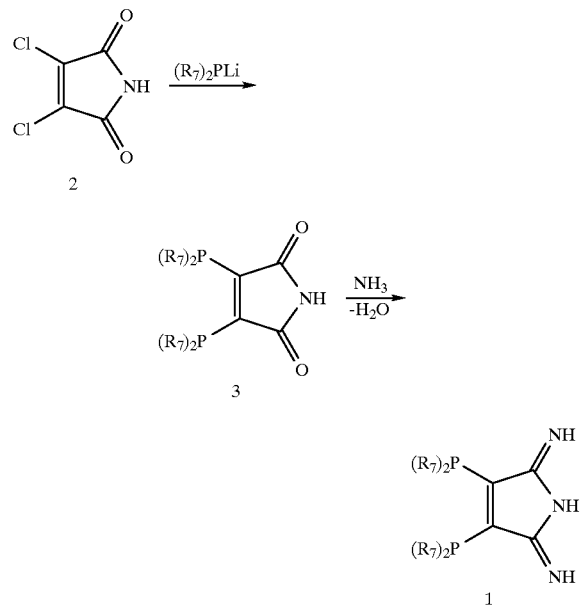

Porphyraine compounds V in the following classes of compounds XXVIII–XXXII have been prepared.

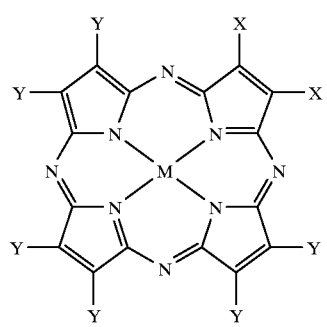

(XXVIII)

-continued

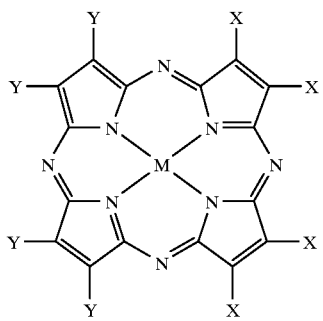
(XXIX)

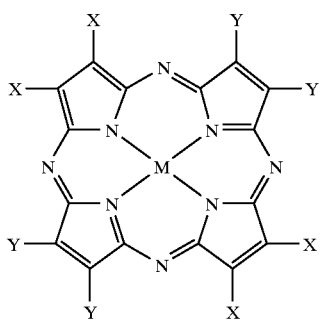
(XXX)

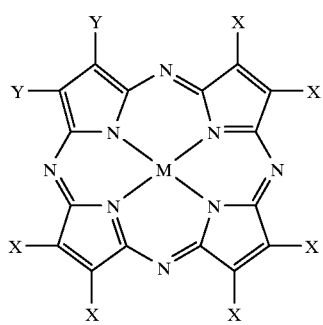
(XXXI)

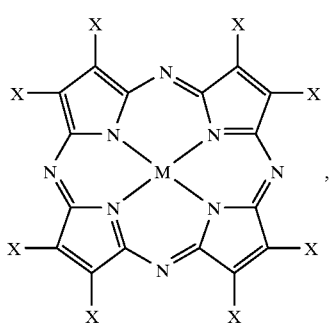
(XXXII)

wherein X is S⁻, SH, $NR_1R_2$ or adjacent X groups are taken together and are S, O or $NR_1$ and a portion of a crown ether; and Y is phenyl, 4-tertiary butyl phenyl, or adjacent Y groups are taken together and are benzo or 3,4-dialkyloxybenzo, excluding compound XXXII when X is sulfur.

For example, the following compounds of structural formula XXVIIIa, XXIXa and XXXa, which correspond to compounds XXVIII, XXIX and XXX, respectively, have been synthesized and characterized. For each compound XXVIIIa through XXXa, compounds wherein M is 2H, Mg, Ni or MnCl have been prepared.

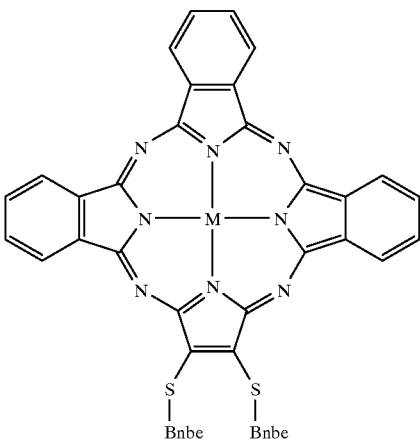
(XXVIIIa)

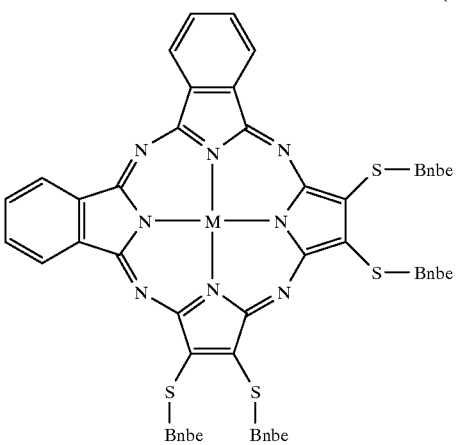
(XXIXa)

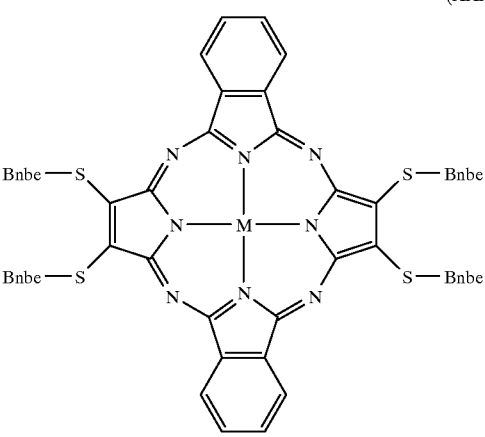
(XXXa)

Compounds XXVIII–XXXII can be reacted with metal salts or metal coordination compounds to provide multimetallic porphyrazine compounds VI–X. The multimetallic porphyrazine compounds can be used as dye materials or as imaging agents. In addition, the multimetallic porphyrazine compounds can be used to prepare oligomers and polymers utilizing metal ion coordination chemistry to link individual or oligomeric multimetallic porphyrazine compounds in a predetermined array. The multimetallic porphyrazine compounds also can be coordinated with a substrate to form a complex. The substrate can be a polymer, an inorganic solid or glass, or can be an antibody.

In particular, the porphyrazine compounds of the present invention permit conversion of a compound XXVIII, after conversion to a multimetallic porphyrazine compound by complexing a metal ion to the periphery of porphyrazine compound, into a dimacrocyclic trimetallic array by edge-sharing the peripherally complexed metal ion ($M^1$) between adjacent porphyrazine units, illustrated as compound I. Any of the compounds in classes XXIX–XXXII, after conversion into a multimetallic porphyrazine compound, then can be converted into clusters by multiple edge sharing of peripherally complexed metal ions. The compounds of class XXX provide linear ribbon polymers by coordination polymerization with $M^1$ metal ions complexed on the periphery of the compound. The compounds of class XXXII similarly provide two-dimensional, sheet polymers.

In particular, the compounds XXVIII, XXIX and XXX, wherein X is SH, M is nickel(II) or copper(II), and Y is benzo, phenyl or 4-t-butylphenyl have been prepared and converted into a multimetallic compound, such as the compound having the structural formula XXXIII.

The compound having structural formula XXXIV, wherein X is S, O, or NH, also has been prepared and macrocyclized to provide a tetra-crowned porphyrazine compound V and a mono-crowned porphyrazine compound V.

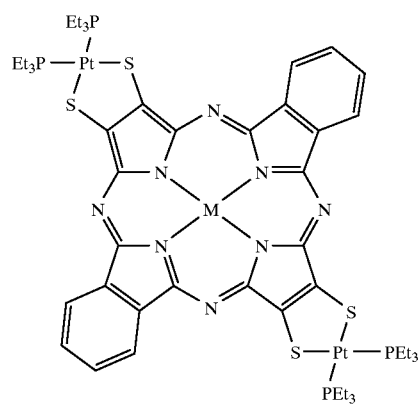

(XXXIII)

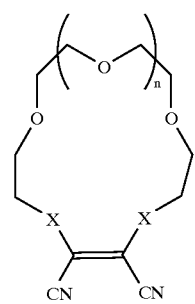

(XXXIV)

The tetra-crowned porphyrazine based on compound XXXIV, wherein X is S, was converted into a multimetallic complex by interaction with a metal ion salt, as exemplified in the compound of structural formula XXXV.

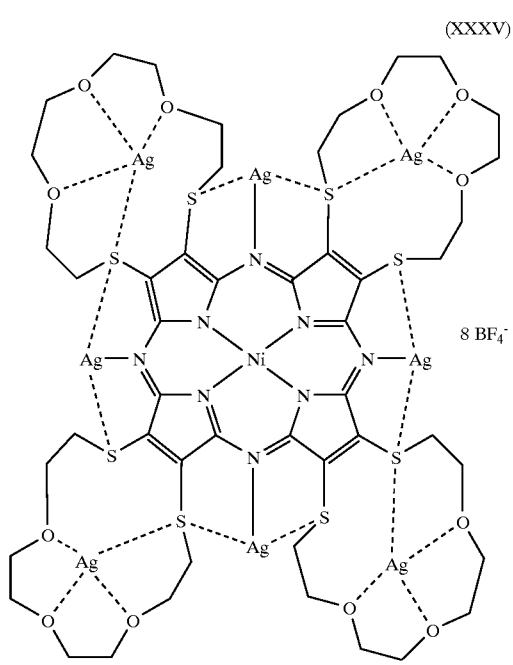

(XXXV)

Other multimetallic porphyrazine compounds prepared from a porphyrazine compound V include, for example:

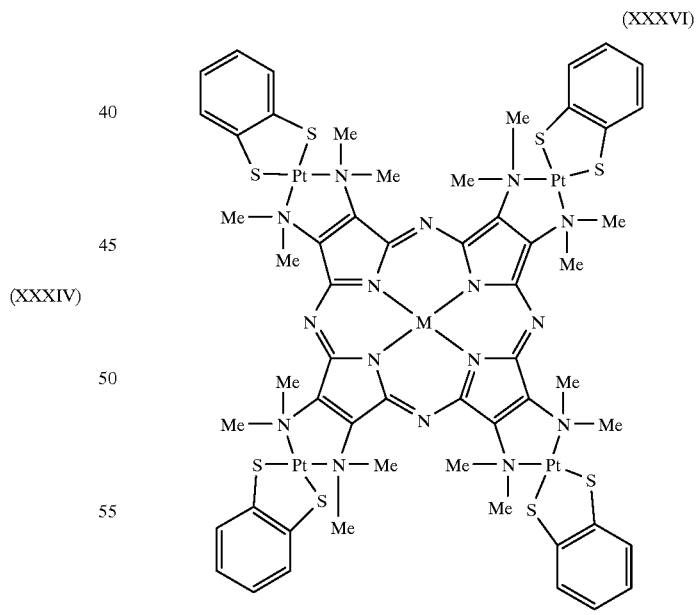

(XXXVI)

-continued

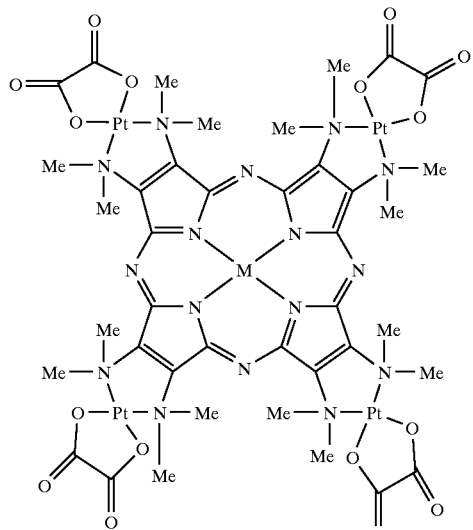

(XXXVII)

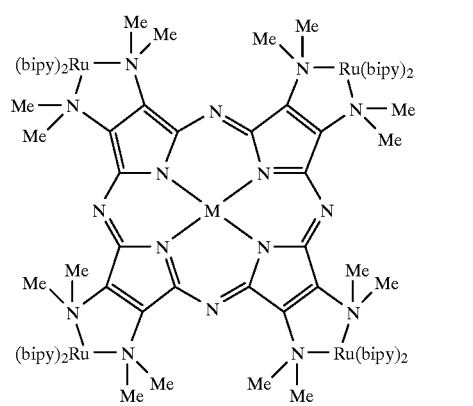

(XXXVIII)

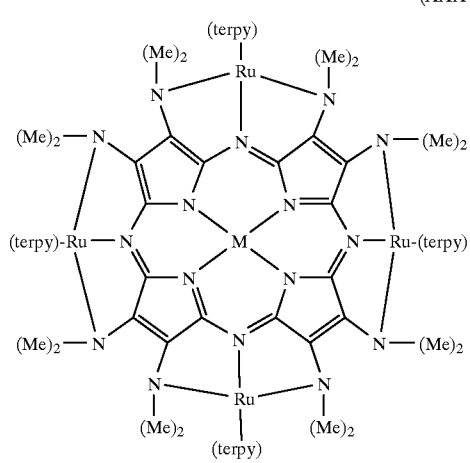

(XXXVIIIa)

wherein M is Ni(II), Cu(II), Mn(II), bipy is bipyridyl, terpy is terpyridyl, and Me is methyl.

The porphyrazine compounds V are converted into multimetallic porphyrazine compounds by methods well known in the art. For example, a porphyrazine compound V is reacted with either (a) $NiCl_2 \cdot 6H_2O$ in ethanol (EtOH), (b) $CrCl_3$ $(THF)_3$ (THF, tetrahydrofuran) and $Ph_3PBn^+Cl^-$ (Ph, phenyl; Bn, benzyl) or (c) $MnI_2$ in methylene chloride ($CH_2Cl_2$) to provide the corresponding multimetallic porphyrazine complexed peripherally with Ni(II), Cr(III) or Mn(II).

The multimetallic porphyrazine XXXVI was prepared by reacting porphyrazine XVII, wherein $R_1$ and $R_2$ are methyl, with potassium hexachlorplatinate ($K_2PtCl_6$) and hydrazine, followed by a reaction with 1,2-benzenedithiol and sodium hydride. The multimetallic porphyrazine of structural formula XXXVII was prepared in the identical manner, except the intermediate tetrakis (dichloroplatino) complex was intercepted by oxalate anion.

In general, any transition metal, lanthanide, actinide, alkali metal, Group IIIB and IVB element or alkaline earth metal can be complexed at the periphery of a porphyrazine compound V. Specific metal ions $M^1$ complexed at the periphery of the porphyrazine compounds include, but are not limited to, Pt, Sn, Ni, Hg, Zn, Mn, Cu, Cr, Fe, Gd, Si, Mo, Ru, Rh, Mg, Ti, V, Pd, Cd, Au, Tc, Eu, Sm, Ce, Ga, and Th.

As set forth above, compound I is an oligomer linked by edge-sharing a peripherally complexed $M^1$ metal ion. The porphyrazine compounds V, therefore, can be converted into multimetallic, multimacrocyclic arrays by complexing one metal ion within each macrocyclic cavity and an additional one to four metal ions to the peripheral amino, oxo, phospho, thio, seleno and/or telluro moieties of the porphyrazine compound. Multimetallic porphyrazine compounds VI–X are assembled into polymacrocyclic arrays of predetermined structure by a link up of peripherally complexed metal ions in a controlled oligomerization or polymerization.

Oligomers having a structural formula I have been prepared. These oligomers incorporate copper(II), magnesium or nickel(II) as the element complexed within the macrocyclic cavity, and the individual multimetallic porphyrazine compounds are linked by peripherally complexed platinum or tin. Nonlimiting oligomers are illustrated in structures XXXIX and XL, wherein Me is methyl and Y is 4-t-butylphenyl or the two Y groups are taken together as benzo.

(XXXIX)

(XL)

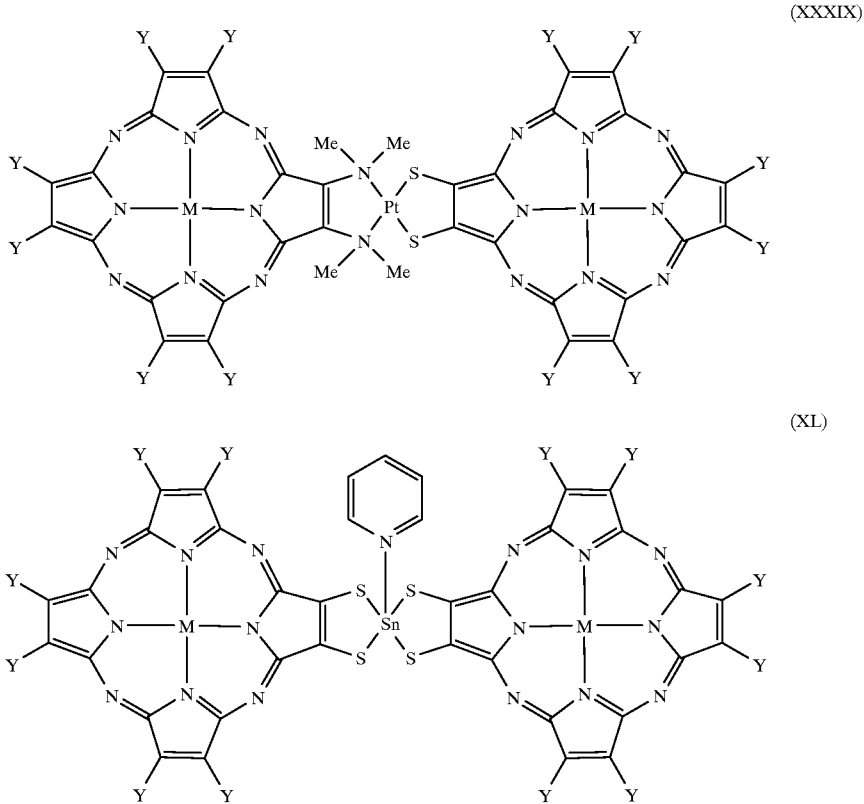

Other linking metal ions, in addition to platinum and tin, include, but are not limited to, Cr, Ni, Mn, Hg, Zn, Cu, Fe, Gd, Si, Mo, Ru, Rh, Co, Pd, Ti, V and Ga.

It should be noted that the porphyrazine oligomer, overall, can be neutral, cationic or anionic in character. The electronic character of the porphyrazine oligomer is dependent on the identity of porphyrazine V, the identity and coordination state of the linking metal ion $M_1$, and the ligand or counterion associated with the linking metal ion $M_1$.

By replacing the Y hydrocarbon groups in compounds XXXIX and XL with amino, sulfo, oxo, phospho, seleno or telluro moieties, the oligomers can be extended linearly to form a ribbon polymer, or can be extended in two dimensions to form a sheet polymer. An oligomer synthesis is illustrated below, wherein the porphyrazines V are depicted in shorthand notation wherein

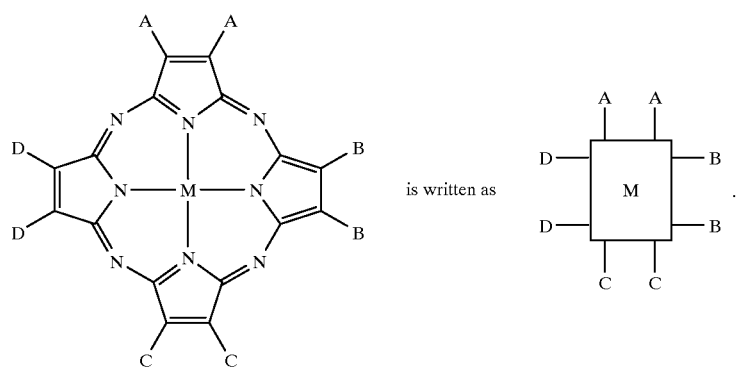

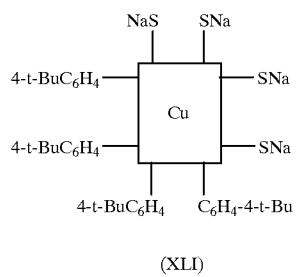

(XLI)

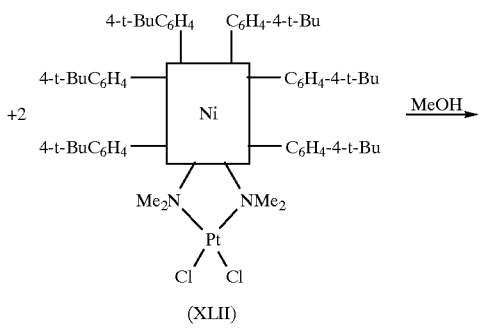

(XLII)

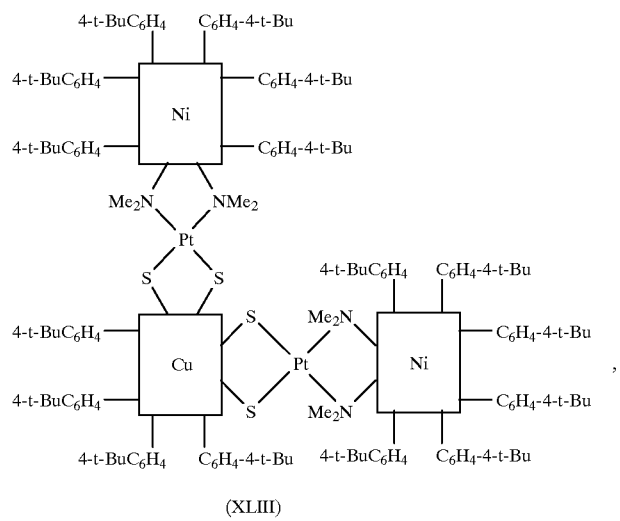

(XLIII)

wherein 4-t-BuC$_6$H$_4$ is 4-tert-butylphenyl, MeOH is methanol, and Me is methyl.

In the preparation of oligomer XLIII, the tetrathiolate porphyrazine XLI is reacted with the multimetallic platinum (II) chloride porphyrazine compound XLII to produce the corresponding pentametallic trimacrocyclic oligomer XLIII by edge-sharing of the peripherally complexed platinum ions. Identical reaction schemes are used to produce the nonametallic compound XLIV,

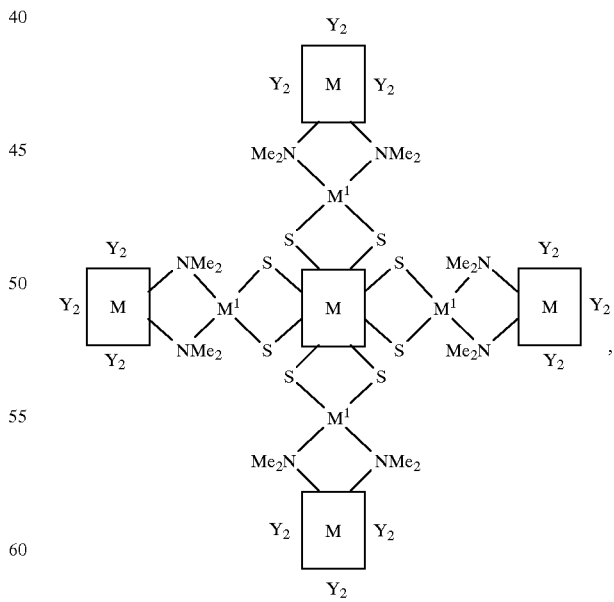

(XLIV)

or the ribbon polymers XLV and XLVI, wherein Y$_2$ is benzo, M is Ni(II), Cu(II) or Mn(II),

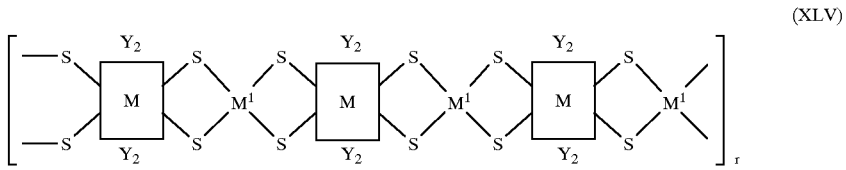

(XLV)

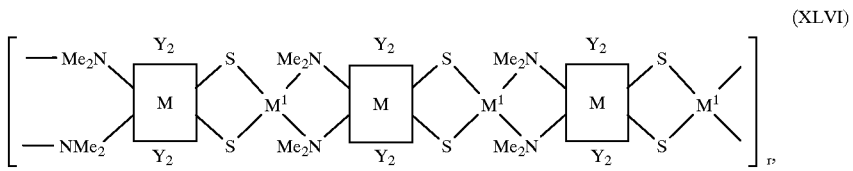

(XLVI)

$M^1$ is Pt(II) or Ni(II), and r is an integer 1, for example. The integer r however can be 1 through 1,000. $Y_2$ also can be phenyl, polyethyleneoxo or an alkyl group having one to 12 carbon atoms.

Also envisioned are the ribbon polymers of structural formulae XLVII and XLVIII, which have nonporphyrazine ligand-metal spacers (e.g., 1,2,4,5-benzenetetrathiol or 1,2,4,5-tetrakis(diphenylphosphino)benzene).

The resulting polymers can be used as molecular conductors and magnets. The polymers are made conductive by doping, either through the use of molecular oxidants (e.g., I2) or through electro-oxidation, and using either "innocent" (i.e., nonconducting) molecular or polymeric cations or cations that are conductors (e.g., tetramethyltetra-selenofulvalene (TMTSF$^+$))

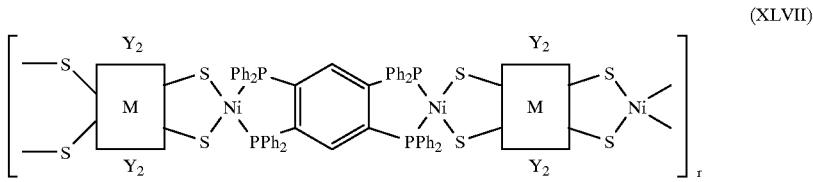

(XLVII)

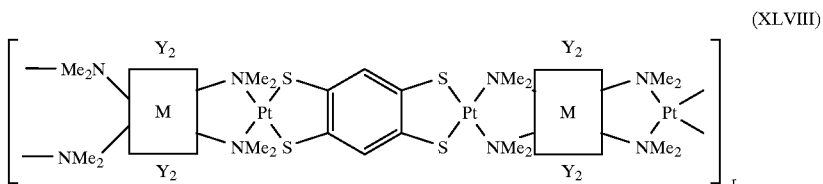

(XLVIII)

Sheet polymers also can be prepared from porphyrazine compounds V wherein all eight of the A, B, C, and D moieties are capable of complexing metal ions to the periphery of the compound, such as the porphyrazine having structural formula IL. The porphyrazine IL can be reacted with a platinum

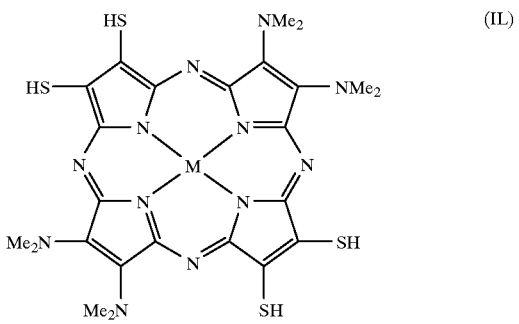

(IL)

compound, or other metal capable of complexing with sulfur or nitrogen atoms, to form a two-dimensional sheet polymer. The sheet polymers can be prepared as a film.

The porphyrazine compounds V, and the multimetallic porphyrazines, oligomers, ribbon polymers and sheet polymers produced therefrom, have a wide variety of practical applications because essentially any metal ion can be complexed in the macrocyclic core, or at the periphery of porphyrazine compound V. The selection of different metals provides compounds, oligomers and polymers having a wide variety of physical and chemical properties. For example, porphyrazine compounds V having mixed valence states are achievable. Such mixed valence compounds will have applications in redox chemistry, such as in redox/oxygenation catalysts. The porphyrazine compounds V, and polymers therefrom, also exhibit magnetic properties suitable for magnet materials. In addition, the substitution of various metals at the periphery and the core of the porphyrazine compounds V provide different colored multimetallic complexes VI–X which are the basis of a variety of dyes.

The porphyrazine compounds V, and multimetallic porphyrazine compounds VI–X provided therefrom, have numerous practical applications. For example, a multimetallic porphyrazine compound VI–X having oxo moieties and complexed with paramagnetic metals, such as copper or vanadium, both within the macrocyclic core and at the periphery of the compound, are ultra high-spin molecules having potential application as building blocks for molecular ferromagnets or as contrast agents in magnetic resonance imaging (MRI). Porphyrazine compounds V having amino moieties exhibit a mixed valency when a transition metal is complexed to the periphery of the compound. Accordingly, complexing multiple transition metals and rare earth metals to a porphyrazine compound V can yield MRI imaging agents.

For multimetallic porphyrazine compounds VI–X, when the metal ion complexed in the macrocyclic core is catalytically active, i.e., iron or manganese, and when the metal ions complexed to the peripheral moieties are redox active, the compound VI–X can be an efficient redox/oxygenation catalyst with built-in pathways for supplying or removing electrons by electrochemistry and/or photocatalysis.

Porphyrazine compounds V also can be used to complex both redox-active metals and alkali metal ions, thereby having potential use as ionophores and ion-selective reagents. Porphyrazine compounds V having crown ethers as the A, B, C, and/or D moieties are especially useful ionophores or ion-selection reagents, as would be porphyrazine compounds V having amino moieties because the compounds having amino moieties are soluble in solvents ranging from hexane to acetonitrile to methanol.

Porphyrazine compounds V and the multimetallic porphyrazine compounds VI–X also serve as building blocks for new molecular metals. The porphyrazine compounds VI–X form oligomers and polymers by edge sharing peripherally complexed metal ions, are soluble in organic solvents, are readily oxidized, show strong coupling interchange, and can be electrocrystallized with a wide range of counter ions and central metal ions to provide novel, partially oxidized, molecular metals. For example, porphyrazine compounds V having two amino and six hydrocarbon moieties have an excellent solubility in organic solvents and are readily oxidized, making them easy to electrocrystallize. Porphyrazine compounds V having trithiocarbonate moieties, such as compound L exhibits strong interchain coupling.

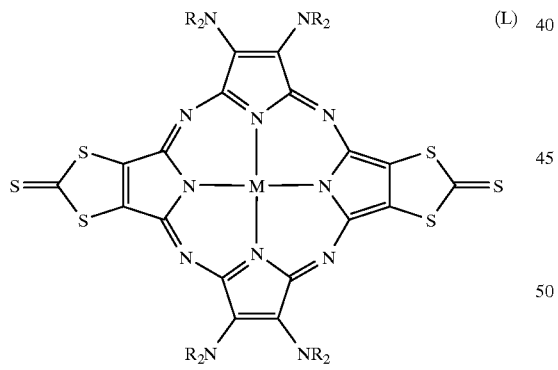

(L)

The multimetallic porphyrazines VI–X also can be used in a high-$T_c$ ferrimagnet.

In accordance with an important feature of the present invention, the porphyrazine compounds depicted in structural formula V can be modified to increase the water solubility of the prophyrazines. In particular, one or more of the A, B, C, and D moieties, whether coordinating or noncoordinating, of the prophyrazines of structural formula V can be modified to position hydrophilic functionalities on the moieties.

As set forth above, the individual A, B, C, and D moieties can contain one or more of the R through $R_{19}$ substituents, which are either hydrogen or an organic substituent bonded to a hydrocarbon moiety or to a heteroatom selected from the group consisting of sulfur, oxygen, nitrogen, phosphorus, selenium, and tellurium. After preparing a porphyrazine compound of structural formula V, the substituents depicted as R through $R_{19}$ can be modified to increase the water solubility of the porphyrazine. Alternatively, the porphyrazine can be synthesized using A, B, C, and D moieties having modified R through $R_{19}$ substituents.

In one embodiment, an R through $R_{19}$ substituent present on an A, B, C, and/or D moiety is a polyethyleneoxy substituent having the formula $-(CH_2CH_2-O)_a-CH_2CH_2OH$, wherein a is zero to nineteen. The hydroxyl group of the polyethyleneoxy substituent can be modified by well-known reactions to increase the water solubility of the porphyrazine. The modification can be performed before or after the A, B, C, or D moiety is positioned on the porphyrazine.

For example, the polyethyleneoxy substituent can be modified by well-known reactions to have the formula

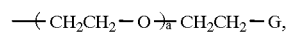

wherein G is selected from the group consisting of

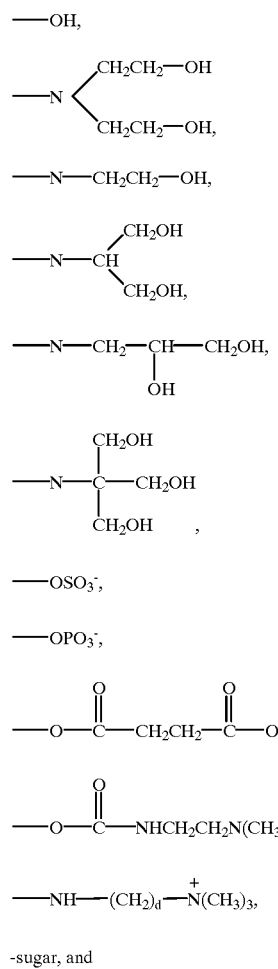

—O—sugar, wherein the sugar can be glucose, galactose, fructose, mannose, and trehalose, as non-limiting examples, like
—β-D-glucopyranosy, and —α-D-glucopyranosyl, and a is an integer 0 to 19, and d is an integer 1 to 5.

In another nonlimiting embodiment, the R through $R_{19}$ substituent can be

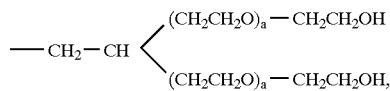

wherein a has been defined previously.

This substituent can be modified to provide the following substituents:

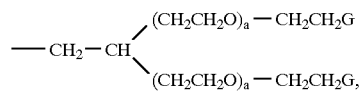

wherein a and G have been previously defined.

Additional hydrophilic R through $R_{19}$ substituents can be positioned on the A, B, C, and/or D moieties of porphyrazine V. For example, the R through $R_{19}$ substituent can be

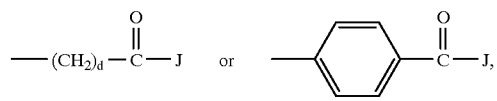

wherein d has been defined previously, and nonlimiting examples of J are —OH,

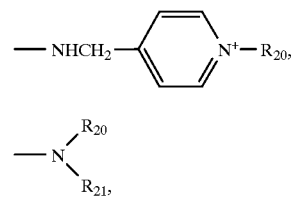

wherein d has been defined previously, and $R_{20}$ and $R_{21}$ are selected, independently, from the group consisting of hydrogen, $C_1$–$C_3$ alkyl, and $C_1$–$C_3$ hydroxyalkyl, for example, —$CH_2CH_2OH$.

Hydrophilic substituents R through $R_{19}$ also can be a substituent having the formula

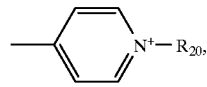

wherein $R_{20}$ has been defined previously.

An example of a porphyrazine compound of structural formula V having modified substituents R through $R_{19}$ is

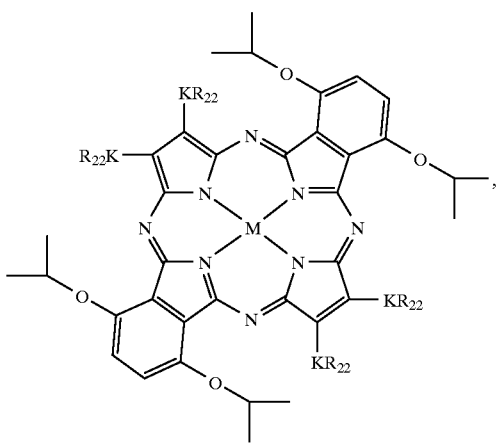

wherein K is selected, independently, from the group consisting of O, S and $NR_{22}$, and $R_{22}$ is selected, independently, from the group consisting of

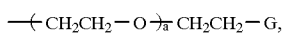

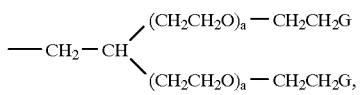

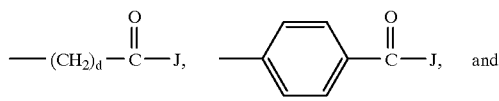

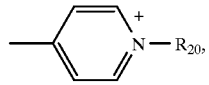

wherein G, J, a, d, and $R_{20}$ have been previously defined.

Another example of a porphyrazine compound of structural formula V having modified substituents R through $R_{19}$ is

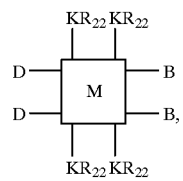

wherein $R_{22}$ has been defined previously, and B and D, independently, are selected from the group consisting of

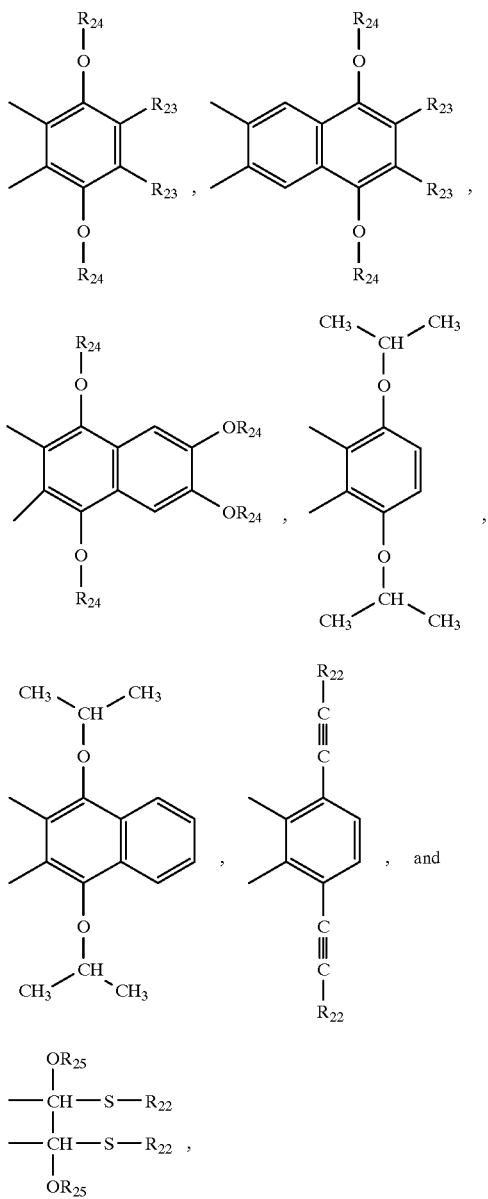

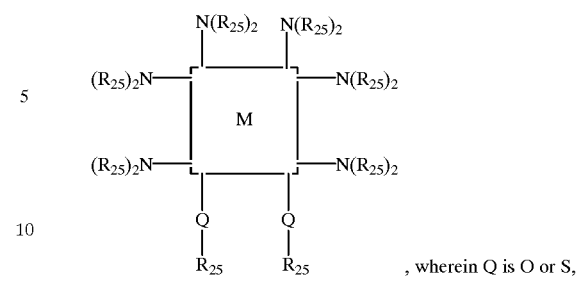, wherein Q is O or S, and $R_{25}$ was defined previously.

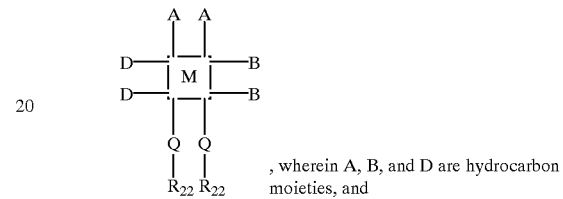, wherein A, B, and D are hydrocarbon moieties, and

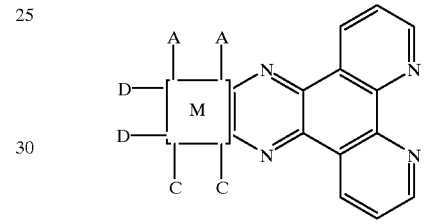

wherein at least one of A, C, and D is taken together to form a ring, and is selected, independently, from

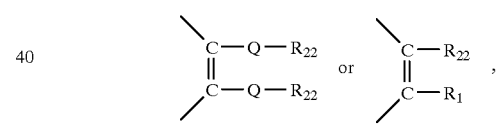

wherein Q, $R_{22}$, and $R_1$ have been defined previously.

wherein $R_{22}$ has been defined previously, $R_{23}$ is hydro, chloro, phenyl, $C_1$–$C_{16}$ alkyl, $C_1$–$C_{12}$ alkylphenyl or —$OR_{22}$, $R_{24}$ is $C_1$–$C_5$ alkyl or $R_{22}$, and $R_{25}$, independently, is $R_1$, $R_2$, or $R_{22}$, each of which was defined previously.

Nonlimiting examples of porphyrazine compounds having improved water solubility include:

Obviously, many modifications and variations of the invention as hereinbefore set forth can be made without departing from the spirit and scope thereof and, therefore, only such limitations should be imposed as are indicated by the appended claims.

What is claimed is:

1. A heteroatom-functionalized porphyrazine compound having the structure:

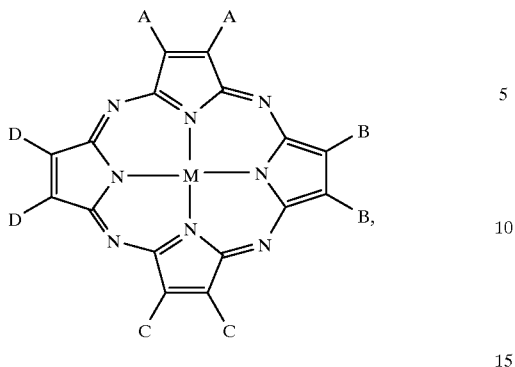

wherein M is 2H or an element capable of complexing with pyrrole nitrogen atoms, and A, B, C and D are independently selected from the group consisting of:
(a) a thio moiety, said thio moiety selected from the group consisting of sulfo; sulfhydryl; alkylthio (—SR), wherein R is an alkyl group having one to 10 carbon atoms, a polyethylene oxide chain having one to twenty ethylene oxide units, phenyl, benzyl or allyl, or R is a benzyl blocking group; —SSi($R_7$)$_3$, wherein the $R_7$ groups are independently selected from an alkyl group having one to 16 carbon atoms and phenyl; —SCH$_2$(CH$_2$)$_c$O (CH$_2$(CH$_2$)$_c$O)$_d$R$_9$ or —SCH$_2$(CH$_2$)$_c$S—(CH$_2$(CH$_2$)$_c$O)$_d$R$_9$, wherein c is one or two, d is an integer from one to five, and $R_9$ is hydrogen or an alkyl group having one to 16 carbon atoms; —SCH$_2$(CH$_2$)$_c$ E(CH$_2$(CH$_2$)$_c$F)$_d$R$_9$, wherein E and F are independently selected from the group consisting of selenium, tellurium, alkylamino wherein the alkyl group has one to 16 carbon atoms, alkyl wherein the alkyl group has two to ten carbon atoms, p-toluene-sulfonamide, 2-pyridylmethyl, COCH$_2$COR$_9$, CH$_2$COCH$_2$COR$_9$, CH$_2$CO$_2$H, and acetamide; trithiocarbonate; and —S—(CH$_2$—S)$_q$—, —S—(CH$_2$CH$_2$—S)$_q$—, or —S—(CH$_2$CH$_2$CH$_2$—S)$_q$—, wherein q is an integer from 2 through 6;
(b) an amino moiety, said amino moiety selected from the group consisting of

wherein $R_1$ and $R_2$ are independently selected from the group consisting of hydrogen, an alkyl group having one to 16 carbon atoms, 2-pyridylmethyl, benzyl, allyl, —CH$_2$CO$_2$H, —COCH$_2$OR$_{15}$, and —CH$_2$OCCH$_2$COR$_{15}$ wherein $R_{15}$ is an alkyl group having one to 16 carbon atoms; —NR$_{16}$—(CH$_2$)$_q$—NR$_{16}$—; —NR$_{16}$—(CH$_2$CH$_2$CH$_2$NR$_{16}$)$_q$—CH$_2$CH$_2$CH$_2$NR$_{16}$—; —NR$_{16}$—(CH$_2$—NR$_{16}$)$_q$—CH$_2$NR$_{16}$—; and —NR$_{16}$—(CH$_2$CH$_2$NR$_{16}$)$_q$CH$_2$CH$_2$NR$_{16}$—, wherein q is an integer from 2 through 6, and $R_{16}$ is hydrogen, an alkyl group having one to ten carbon atoms, 2-pyridylmethyl, benzyl, allyl, —CH$_2$CO$_2$H, —COCH$_2$OR$_{10}$, or —CH$_2$ OCCH$_2$—COR$_{10}$, wherein $R_{10}$ is an alkyl group having one to 12 carbon atoms;
(c) an oxo moiety, wherein said oxo moiety is selected from the group consisting of:
hydroxyl; alkoxy (—OR$_{17}$); acyloxy (—OCOR$_{17}$) silyloxy (—OSi (R$_{17}$)$_3$), wherein $R_{17}$ is an alkyl group having one to 12 carbon atoms, benzyl or phenyl; a ring containing at least two oxygen atoms; a ring containing at least one oxygen atom and either one nitrogen, sulfur, phosphorus, tellurium or selenium atom; carbonate; —O—((cH$_2$)$_t$—X)$_v$—O—, wherein X is sulfur, oxygen, phosphorus, selenium, tellurium, or —NR$_{11}$, wherein $R_{11}$ is selected from the group consisting of hydrogen, an alkyl group having one to six carbon atoms, 2-pyridylmethyl, benzyl, allyl, —CH$_2$CO$_2$H, —COCH$_2$OR$_{10}$, and —CH$_2$OCCH$_2$COR$_{10}$, wherein $R_{10}$ is an alkyl group having one to twelve carbon atoms, v is an integer 1 through 6, and t is an integer 1 through 3; and a ring having the structure

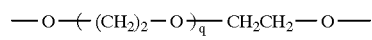

wherein q is an integer from 2 through 6, and wherein the oxygen atoms can be substituted, individually or collectively, with nitrogen, sulfur, phosphorus, tellurium or selenium;
(d) a phospho moiety, wherein the phospho moiety is selected from the group consisting of alkylphosphino (—PR$_3$R$_4$), wherein $R_3$ and $R_4$ can be the same or different and are alkyl groups having one to 12 carbon atoms, benzyl, phenyl, polyethyleneoxy or polyphenyl ether; a phosphonate ester (P(OR$_5$))$_2$, wherein $R_5$ is an alkyl group having 1 to 12 carbon atoms or phenyl;

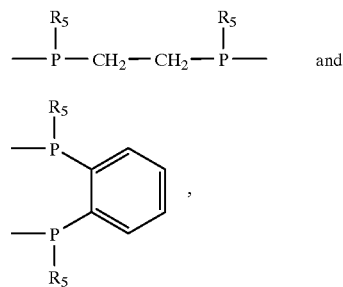

wherein $R_5$ is hydrogen, an alkyl group having 1 to 3 carbon atoms or phenyl;
(e) a seleno moiety;
(f) a telluro moiety, wherein the seleno moiety or telluro moiety is selected from the group consisting of seleno (—SeH or —Se$^-$); telluro (—The or Te_); alkylseleno; alkyltelluro (—Se(Te)R$_6$), wherein $R_6$ is an alkyl group having one to 12 carbon atoms, allyl, phenyl or benzyl; —Se(Te)M$^2$, wherein M$^2$ is an alkali metal ion or an alkaline earth metal ion; —Se(Te)Si(R$_7$)$_3$, wherein the $R_7$ groups are independently selected from an alkyl group having one to 12 carbon atoms and phenyl; —Se(Te)CH$_2$C$_6$H$_4$-4-CO$_2$R$_8$, $R_8$ is an alkyl group having one to six carbon atoms or phenyl; —Se(Te)CH$_2$(CH$_2$)$_c$O(CH$_2$(CH$_2$)$_c$ O)$_d$R$_9$; —Se(Te)—CH$_2$(CH$_2$)$_c$S(CH$_2$(CH$_2$)$_c$O)$_d$R$_9$ wherein c is one or two, d is an integer from one to five, and $R_9$ is hydrogen or an alkyl group having one to 12 carbon atoms; and —Se(Te)CH$_2$—(CH$_2$)$_c$E (CH$_2$(CH$_2$) $_c$F)$_d$R$_9$ wherein E and F are independently selected from the group consisting of selenium, tellurium, alkylamino (wherein the alkyl group has one to five carbon atoms), alkyl (wherein the alkyl group has two to ten carbon atoms), 2-pyridylmethyl, —COCH$_2$COR$_9$, —CH$_2$COCH$_2$—COR$_9$, p-toluenesulfonamide and acetamide;

and (g) a hydrocarbon moiety, wherein the hydrocarbon moiety is selected from the group consisting of hydrogen; an alkyl group having one to 18 carbon atoms; phenyl; alkylphenyl; alkoxyphenyl, wherein the alkyl or alkoxy group has one to 12 carbon atoms; benzo; and polyethyleneoxyphenyl;

with the proviso that not all of A, B, C and D are thio moieties and that not all of A, B, C and D are hydrocarbon moieties, and wherein one or more of A, B, C and D is capable of complexing with a metal ion M$^1$, and wherein substituents on one or more of A, B, C, and D are hydrophilic.

2. The compound of claim 1 wherein at least two of A, B, C, and D are capable of complexing with the metal ion M$^1$.

3. The compound of claim 1 wherein at least three of A, B, C, and D are capable of complexing with the metal ion M$^1$.

4. The compound of claim 1 wherein A, B, C, and D each are capable of complexing with the metal ion M$^1$.

5. The compound of claim 1 wherein A and B are capable of coordinating with the metal ion M$^1$.

6. The compound of claim 1 wherein A and C are capable of coordinating with the metal ion M$^1$.

7. The compound of claim 1 wherein M is selected from the group consisting of two hydrogen atoms, an alkali metal, an alkaline earth metal, a transition metal, a lanthanide, an actinide, aluminum, gallium, indium, thallium, germanium, tin and lead.

8. The compound of claim 1 wherein M is selected from the group consisting of nickel, copper, two hydrogen atoms, magnesium, iron, aluminum, manganese, gadolinium, rhodium, a lanthanide, an actinide, gold, cobalt, platinum, palladium, ruthenium, lead, lithium, zinc, chromium, technetium, silicon, indium, thallium, germanium, tin, tungsten, rhenium, zirconium, iridium, uranium, vanadium, titanium, molybdenum, gallium, neodymium, and ytterbium.

9. The compound of claim 1 wherein the two A moieties, the two B moieties, the two C moieties, or the two D moieties can be taken together to form a ring.

10. The compound of claim 1 wherein M$^1$ is selected from the group consisting of a transition metal, a lanthanide, an actinide, an alkali metal, an alkaline earth metal, aluminum, gallium, indium, thallium, germanium, tin, and lead.

11. The compound of claim 1 wherein M$^1$ is selected from the group consisting of Pt, Sn, Ni, Hg, Ga, Mn, Cu, Cr, Fe, Gd, Si, Zn, Mo, Ru, Rh, Mg, Ti, V, Pd, Cd, Au, Tc, Eu, Sm, Ce, and Th.

12. The compound of claim 1 wherein the hydrophilic substituent of A, B, C, or D has the structure

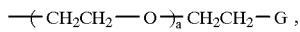

wherein G is selected from the group consisting of

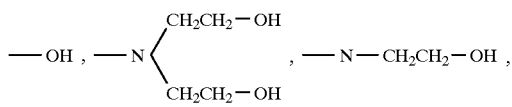

-continued

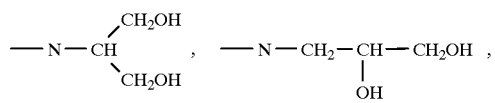

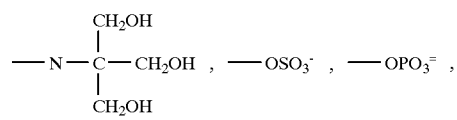

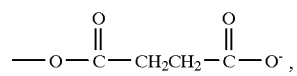

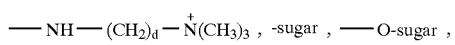

-β-D-glucopyranosyl, and -α-D-glucopyranosyl, and a is an integer 0 to 19, and d is an integer 1 to 5.

13. The compound of claim 1 wherein the hydrophilic substituent of A, B, C, or D has the structure

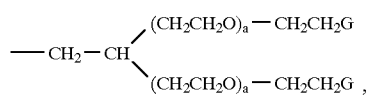

wherein G is selected from the group consisting of

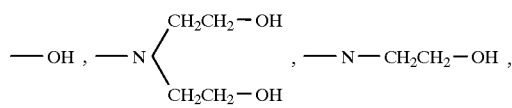

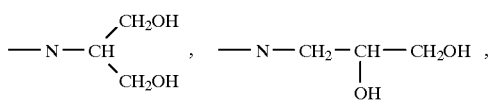

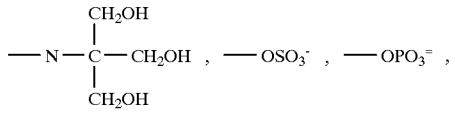

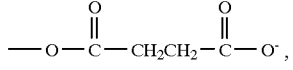

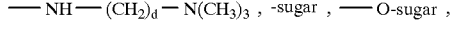

-β-D-glucopyranosyl, and -α-D-glucopyranosyl, a is an integer 0 to 19, and d is an integer 1 to 5.

14. The compound of claim 1 wherein the hydrophilic substituent of A, B, C, or D has the structure:

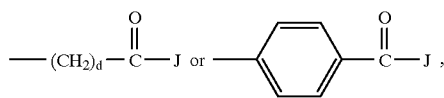

wherein J is selected from the group consisting of

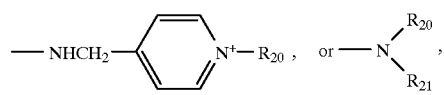

wherein $R_{20}$ and $R_{21}$ are selected, independently, from the group consisting of hydrogen, $C_1$–$C_3$ alkyl, and $C_1$–$C_3$ hydroxyalkyl, and d is an integer 1 to 5.

15. The compound of claim 1 wherein the hydrophilic substitutent of A, B, C, or D has the structure:

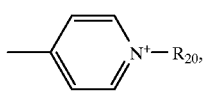

wherein $R_{20}$ is selected from the group consisting of hydrogen, $C_1$–$C_3$ alkyl, and $C_1$–$C_3$ hydroxyalkyl.

16. The compound of claim 1 having the structure

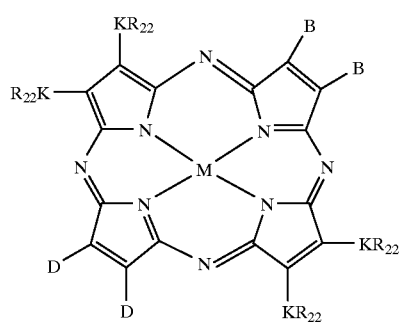

wherein K is selected, independently, from the group consisting of O, S, and $NR_{22}$; $R_{22}$ is selected, independently, from the group consisting of

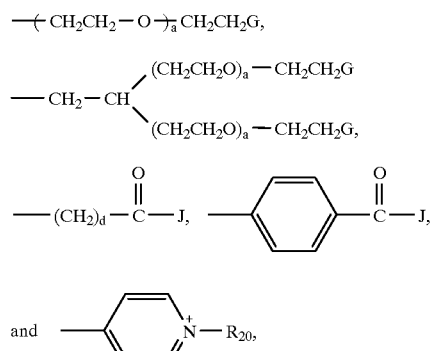

and 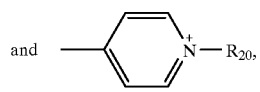

wherein G is selected from the group consisting of

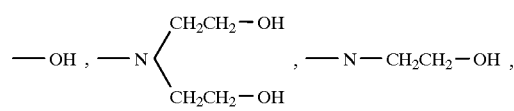

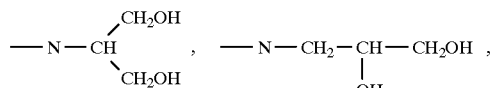

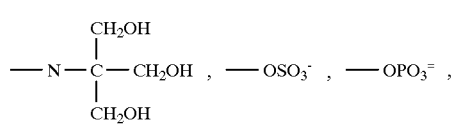

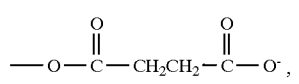

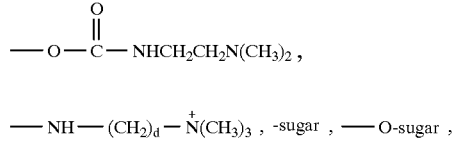

—NH—$(CH_2)_d$—$\overset{+}{N}(CH_3)_3$ , -sugar , —O-sugar ,

-β-D-glucopyranosyl, and -α-D-glucopyranosyl,

J is selected from the group consisting of

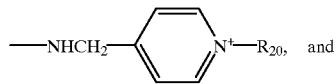 and

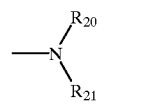

wherein $R_{20}$ and $R_{21}$ are selected, independently, from the group consisting of hydrogen, $C_1$–$C_3$ alkyl, and $C_1$–$C_3$ hydroxyalkyl; a is an integer 0 to 19; d is an integer 1 to 5; and B and D, independently, are selected from the group consisting of

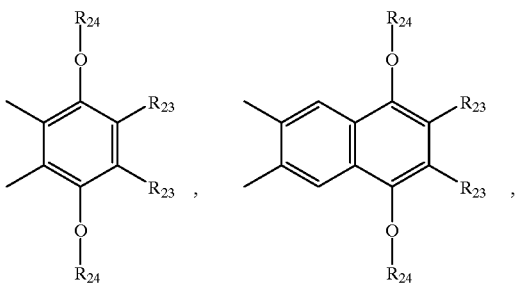

-continued

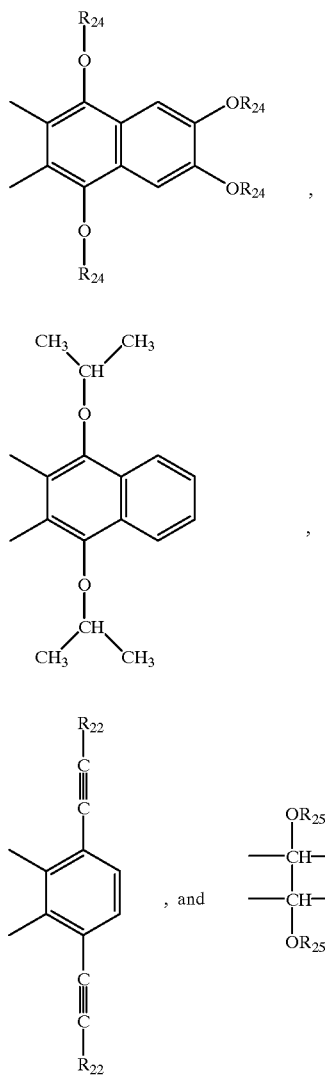

17. The compound of claim 16 having the structure:

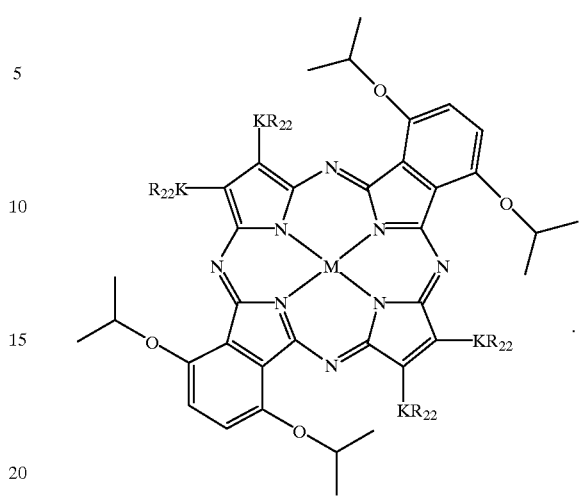

18. The compound of claim 1 having the structure:

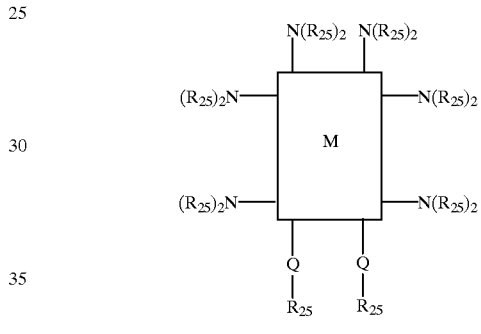

wherein $R_{23}$ is selected from the group hydro, chloro, phenyl, $C_1$–$C_{16}$ alkyl, $C_1$–$C_{12}$ alkylphenyl, and $OR_{22}$, $R_{24}$ is $C_1$–$C_5$ alkyl or $R_{22}$, and $R_{25}$, independently, is selected from the group consisting of an alkyl group having 1 to 16 carbon atoms, 2-pyridylmethyl, benzyl, allyl, —$CH_2CO_2H$, —$COCH_2OR_{15}$, and —$CH_2OCCH_2COR_{15}$, wherein $R_{15}$ is an alkyl group having 1 to 16 carbon atoms.

wherein Q is O or S, and $R_{25}$, independently, is selected from the group consisting of hydrogen, an alkyl group having 1 to 16 carbon atoms, 2-pyridylmethyl, benzyl, allyl, —$CH_2CO_2H$, —$COCH_2OR_{15}$, and —$CH_2OCCH_2COR_{15}$, wherein $R_{15}$ is an alkyl group having 1 to 16 carbon atoms,

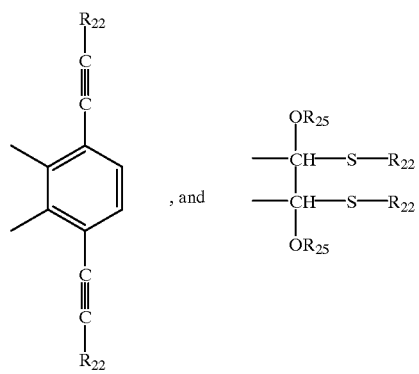, and 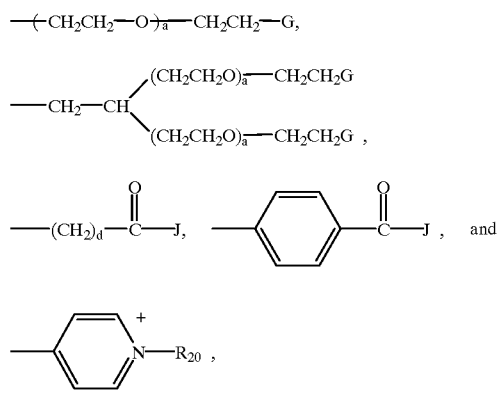

wherein $R_{22}$ is selected from the group consisting of

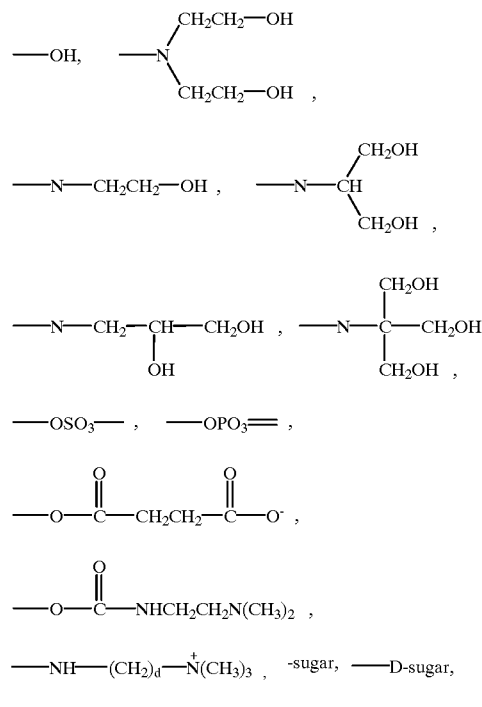

-β-D-glucopyranosyl, and -α-D-glucopyranosyl,

J is selected from the group consisting of

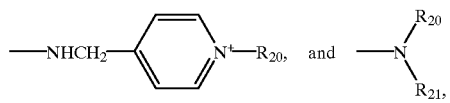

wherein $R_{20}$ and $R_{21}$ are selected, independently, from the group consisting of hydrogen, $C_1$–$C_3$ alkyl, and $C_1$–$C_3$ hydroxyalkyl, a is an integer 0 to 19, and d is an integer 1 to 5.

19. The compound of claim 1 having the structure:

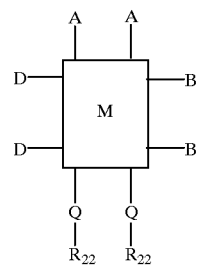

wherein A, B, and D are hydrocarbon moieties, Q is O or S, and $R_{22}$ is selected, independently, from the group consisting of

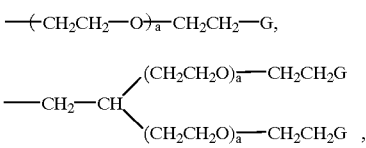

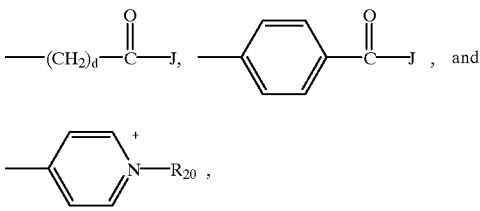

wherein G is selected from the group consisting of

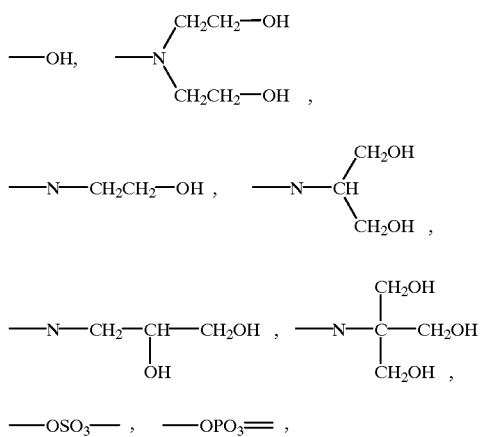

-continued

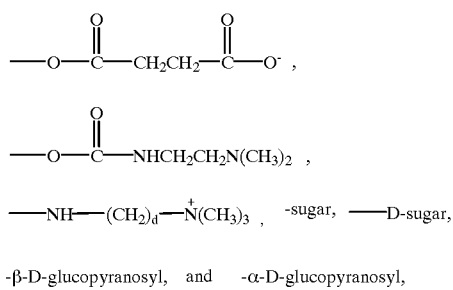

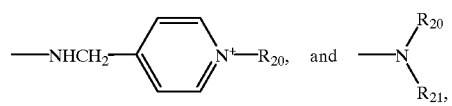

-β-D-glucopyranosyl, and -α-D-glucopyranosyl,

J is selected from the group consisting of

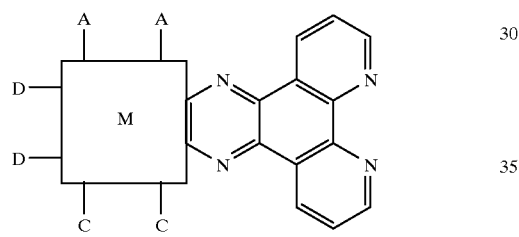

wherein $R_{20}$ and $R_{21}$ are selected, independently, from the group consisting of hydrogen, $C_1$–$C_3$ alkyl, and $C_1$–$C_3$ hydroxyalkyl, a is an integer 0 to 19, and d is an integer 1 to 5.

20. The compound of claim 1 having the structure:

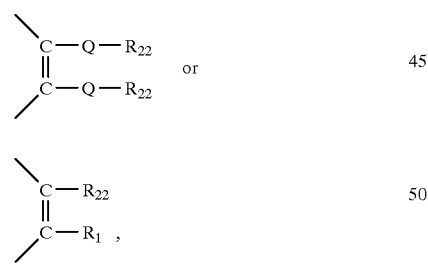

wherein at least one of A, C, and D is taken together to form a ring, and is selected, independently, from

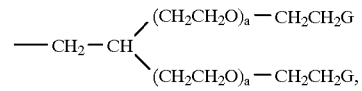 or

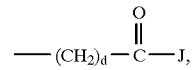, wherein Q is O or S; $R_1$ is selected from the group consisting of hydrogen, an alkyl group having 1 to 16 carbon atoms, 2-pyridylmethyl, benzyl, allyl, —$CH_2CO_2H$, —$COCH_2OR_{15}$, and —$CH_2OCCH_2COR_{15}$, wherein $R_{15}$ is an alkyl group having 1 to 16 carbon atoms; and $R_{22}$ is selected, independently, from the group consisting of —(—$CH_2CH_2$—O.)$_a$—$CH_2CH_2$—G,

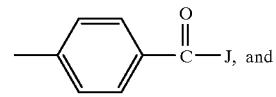

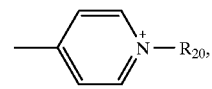

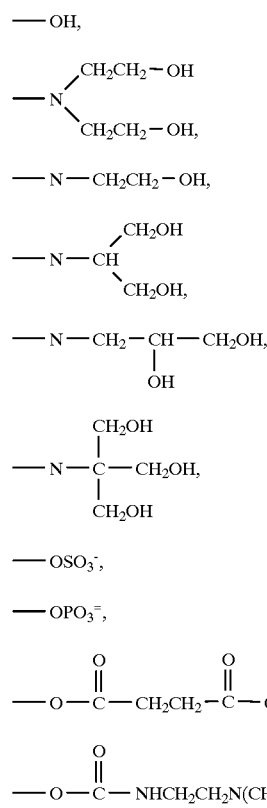

wherein G is selected from the group consisting of

—OH,

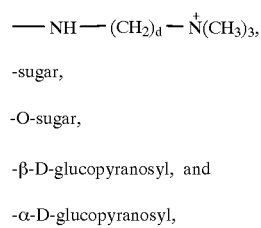

—N—$CH_2CH_2$—OH,

—N—CH(CH_2OH)(CH_2OH),

—N—$CH_2$—CH(OH)—$CH_2OH$,

—N—C(CH_2OH)_2—$CH_2OH$,

—$OSO_3^-$,

—$OPO_3^=$,

—O—C(=O)—$CH_2CH_2$—C(=O)—O⁻,

—O—C(=O)—$NHCH_2CH_2N(CH_3)_2$,

—NH—$(CH_2)_d$—$\overset{+}{N}(CH_3)_3$,

-sugar,

-O-sugar,

-β-D-glucopyranosyl, and

-α-D-glucopyranosyl,

J is selected from the group consisting of

—O⁻

—OR$_{20}$,

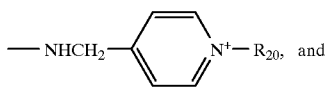

—NHCH$_2$CO$_2{}^-$,
—NH(CH$_2$)$_d$N$^+$(CH$_3$)$_3$, wherein R$_{20}$ and R$_{21}$ are selected, independently, from the group consisting of hydrogen, C$_1$–C$_3$ alkyl, and C$_1$–C$_3$ hydroxyalkyl, a is an integer 0 to 19, and d is an integer 1 to 5.

21. A multimetallic porphyrazine compound comprising a heteroatom-functionalized porphyrazine compound of claim 1 and one or more M$^1$ metal ions complexed to the periphery of the heteroatom-functionalized porphyrazine compound.

22. The multimetallic compound of claim 21 having the structure:

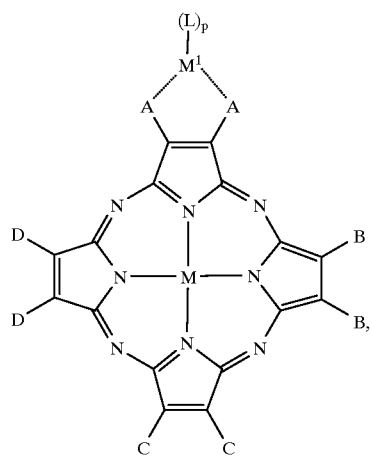

wherein L is a ligand to complete the coordination shell of M$^1$, and integer from 0 through 10.

23. The multimetallic compound of claim 21 having the structure:

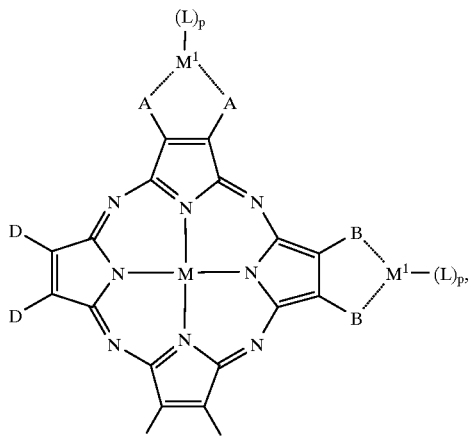

wherein L is a ligand to complete the coordination shell of M$^1$, and p is an integer from 0 through 10.

24. The multimetallic compound of claim 21 having the structure:

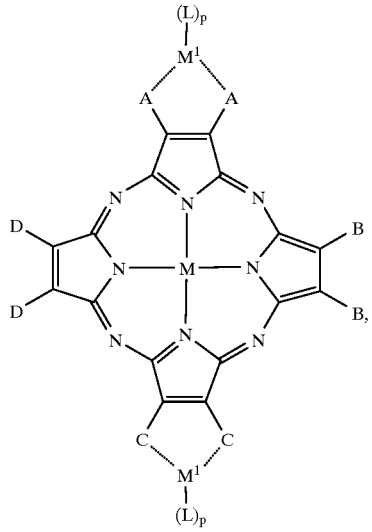

wherein L is a ligand to complete the coordination shell of M$^1$, and p is an integer from 0 through 10.

25. The multimetallic compound of claim 21 having the structure:

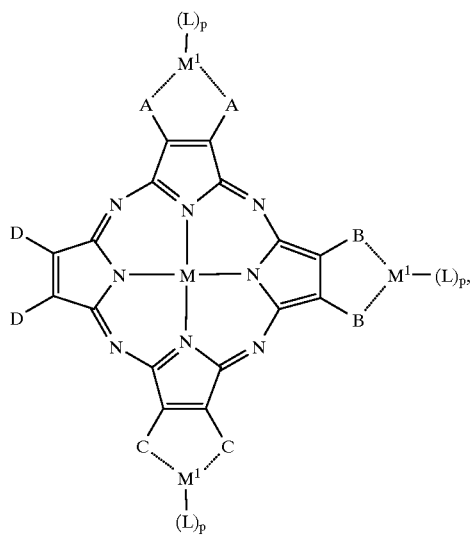

wherein L is a ligand to complete the coordination shell M$^1$, and p is an integer from 0 through 10.

26. The multimetallic compound of claim 21 having the structure:

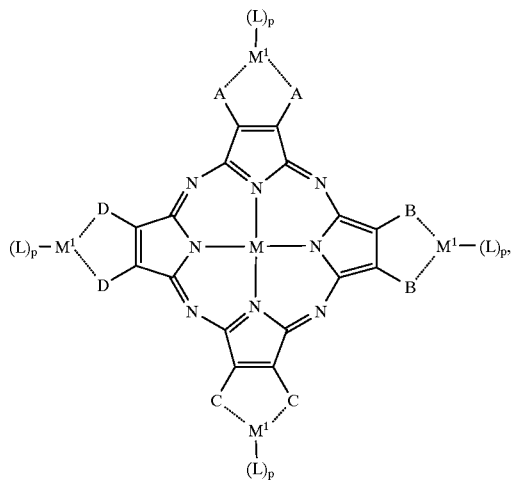

wherein L is a ligand to complete the coordination shell of M¹, and p is an integer from 0 through 10.

27. A heteroatom-functionalized porphyrazine compound having the structure:

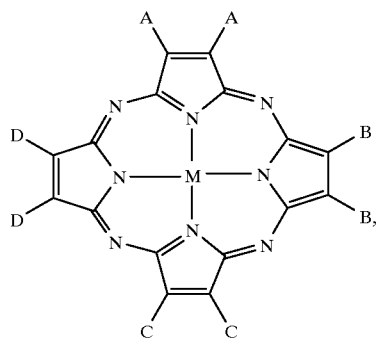

wherein M is 2H or an element capable of completing with pyrrole nitrogen atoms, and A, B, C, and D are independently selected from the group consisting of:
(a) a thio moiety, said thio moiety selected from the group consisting of sulfo; sulfhydryl; alkylthio (—SR), wherein R is an alkyl group having one to 10 carbon atoms, a polyethylene oxide chain having one to twenty ethylene oxide units, phenyl, benzyl or allyl, or R is a benzyl blocking group; —SSi(R$_7$)$_3$, wherein the R$_7$ groups are independently selected from an alkyl group having one to 16 carbon atoms and phenyl; —SCH$_2$(CH$_2$)$_c$O(CH$_2$ (CH$_2$)$_c$O)$_d$R$_9$ or —SCH$_2$(CH$_2$)$_c$S—(CH$_2$(CH$_2$)$_c$O)$_d$R$_9$, wherein c is one or two, d is an integer from one to five, and R$_9$ is hydrogen or an alkyl group having one to 16 carbon atoms; —SCH$_2$(CH$_2$)$_2$E(CH$_2$(CH$_2$)$_c$F$_d$R$_9$, wherein E and F are independently selected from the group consisting of selenium, tellurium, alkylamino wherein the alkyl group has one to 16 carbon atoms, alkyl wherein the alkyl group has two to ten carbon atoms, p-toluene-sulfonamide, 2-pyridylmethyl, COCH$_2$COR$_9$, CH$_2$COCH$_2$COR$_9$, CH$_2$CO$_2$H, and acetamide; trithiocarbonate; and —S—(CH$_2$—S)$_q$—, —S—(CH$_2$CH$_2$—S)$_q$—, or —S—(CH$_2$CH$_2$CH$_2$—S)$_q$—, wherein q is an integer from 2 through 6;
(b) an amino moiety, said amino moiety selected from the group consisting of

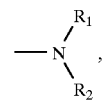

wherein R$_1$ and R$_2$ are independently selected from the group consisting of hydrogen, an alkyl group having one to 16 carbon atoms, 2-pyridylmethyl, benzyl, allyl, —CH$_2$CO$_2$H, —COCH$_2$OR$_{15}$, and —CH$_2$OCCH$_2$COR$_{15}$, wherein R$_{15}$ is an alkyl group having one to 16 carbon atoms; —NR$_{16}$—(CH$_2$)$_q$—NR$_{16}$—; —NR$_{16}$—(CH$_2$CH$_2$CH$_2$NR$_{16}$)$_q$—CH$_2$CH$_2$CH$_2$NR$_{16}$—; —NR$_{16}$—(CH$_2$—NR$_{16}$)$_q$—CH$_2$NR$_{16}$—; and —NR$_{16}$—(CH$_2$CH$_2$NR$_{16}$)$_q$CH$_2$CH$_2$NR$_{16}$—, wherein q is an integer from 2 through 6, and R$_{16}$ is hydrogen, an alkyl group having one to ten carbon atoms, 2-pyridylmethyl, benzyl, allyl, —CH$_2$CO$_2$H, —COCH$_2$OR$_{10}$, or —CH$_2$OCCH$_2$—COR$_{10}$, wherein R$_{10}$ is an alkyl group having one to 12 carbon atoms;
(c) an oxo moiety, wherein said oxo moiety is selected from the group consisting of:
hydroxyl; alkoxy (—OR$_{17}$); acyloxy (—OCOR$_{17}$); silyloxy (—OSi(R$_{17}$)$_3$), wherein R$_{17}$ is an alkyl group having one to 12 carbon atoms, benzyl or phenyl; a ring containing at least two oxygen atoms; a ring containing at least one oxygen atom and either one nitrogen, sulfur, phosphorus, tellurium or selenium atom; carbonate; —O—((CH$_2$)$_t$—X)$_v$—O—, wherein X is sulfur, oxygen, phosphorus, selenium, tellurium, or —NR$_{11}$, wherein R$_{11}$ is selected from the group consisting of hydrogen, an alkyl group having one to six carbon atoms, 2-pyridylmethyl, benzyl, allyl, —CH$_2$CO$_2$H, —COCH$_2$OR$_{10}$, and —CH$_2$OCCH$_2$COR$_{10}$, wherein R$_{10}$ is an alkyl group having one to twelve carbon atoms, v is an integer 1 through 6, and t is an integer 1 through 3; and a ring having the structure

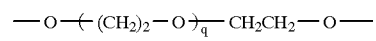

wherein q is an integer from 2 through 6, and wherein the oxygen atoms can be substituted, individually or collectively, with nitrogen, sulfur, phosphorus, tellurium or selenium;
(d) a phospho moiety, wherein the phospho moiety is selected from the group consisting of alkylphosphino (—PR$_3$R$_4$), wherein R$_3$ and R$_4$ can be the same or different and are alkyl groups having one to 12 carbon atoms, benzyl, phenyl, polyethyleneoxy or polyphenyl ether; a phosphonate ester (P(OR$_5$)$_2$, wherein R$_5$ is an alkyl group having 1 to 12 carbon atoms or phenyl;

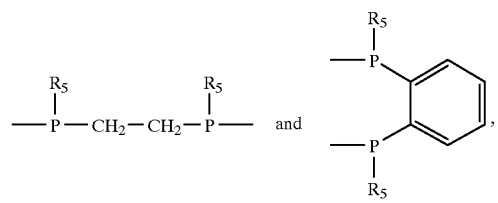

wherein R$_5$ is hydrogen, an alkyl group having 1 to 3 carbon atoms or phenyl;

(e) a seleno moiety;

(f) a telluro moiety, wherein the seleno moiety or telluro moiety is selected from the group consisting of seleno (—SeH or —Se⁻); telluro (—The or Te⁻); alkylseleno; alkyltelluro (—Se(Te)$R_6$), wherein $R_6$ is an alkyl group having one to 12 carbon atoms, allyl, phenyl or benzyl; —Se(Te)$M^2$, wherein $M^2$ is an alkali metal ion or an alkaline earth metal ion; —Se(Te)Si($R_7$)$_3$, wherein the $R_7$ groups are independently selected from an alkyl group having one to 12 carbon atoms and phenyl; —Se(Te)$CH_2C_6H_4$-4-$CO_2R_8$, $R_8$ is an alkyl group having one to six carbon atoms or phenyl; —Se(Te)$CH_2(CH_2)_cO(CH_2(CH_2)_cO)_dR_9$; —Se(Te)—$CH_2(CH_2)_cS(CH_2(CH_2)_cO)_dR_9$, wherein c is one or two, d is an integer from one to five, and $R_9$ is hydrogen or an alkyl group having one to 12 carbon atoms; and —Se(Te)$CH_2$—$(CH_2)_cE(CH_2(CH_2)_cF)_dR_9$, wherein E and F are independently selected from the group consisting of selenium, tellurium, alkylamino (wherein the alkyl group has one to five carbon atoms), alkyl (wherein the alkyl group has two to ten carbon atoms), 2-pyridylmethyl, —$COCH_2COR_9$, —$CH_2COCH_2$—$COR_9$, p-toluenesulfonamide and acetamide;

and (g) a hydrocarbon moiety, wherein the hydrocarbon moiety is selected from the group consisting of hydrogen; an alkyl group having one to 18 carbon atoms; phenyl; alkylphenyl; alkoxyohenyl, wherein the alkyl or alkoxy group has one to 12 carbon atoms; benzo; and polyethyleneoxyphenyl;

wherein one or more of A, B, C, and D is capable of complexing with a metal ion $M^1$, and at least one of A, B, C, and D are oxo moieties, and wherein the oxo moieties are hydroxyl moieties reacted with a diol-protecting group to form a ring having at least two oxygen atoms.

28. The compound of claim 27, wherein the diol-protecting group has the structure:

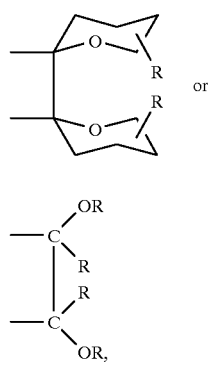

wherein R, selected independently, is an alkyl group having 1 to 10 carbon atoms, a polyethylene oxide chain having 1 to 20 ethylene oxide units, phenyl, benzyl, allyl, or a benzyl-blocking group.

29. The compound of claim 27 having the structure:

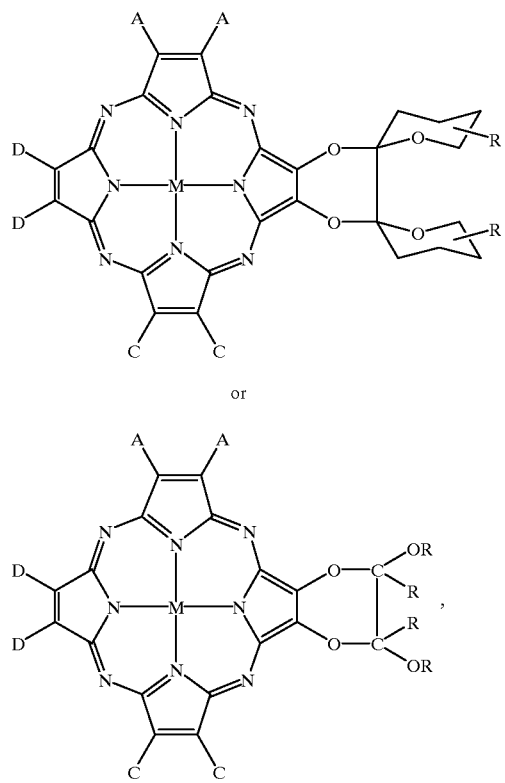

wherein R, selected independently, is an alkyl group having 1 to 10 carbon atoms, a polyethylene oxide chain having 1 to 20 ethylene oxide units, phenyl, benzyl, allyl, or a benzyl-blocking group.

30. A heteroatom-functionalized porphyrazine compound having the structure:

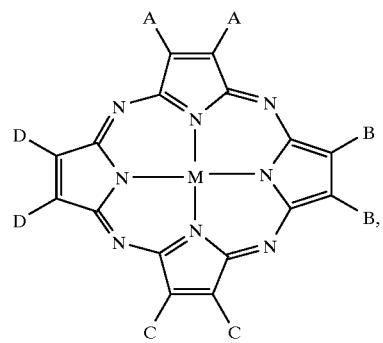

wherein M is 2H or an element capable of complexing with pyrrole nitrogen atoms, and A, B, C, and D are independently selected from the group consisting of:
(a) a thio moiety, said thio moiety selected from the group consisting of sulfo; sulfhydryl; alkylthio (—SR), wherein R is an alkyl group having one to 10 carbon atoms, a polyethylene oxide chain having one to twenty ethylene oxide units, phenyl, benzyl or allyl, or R is a benzyl blocking group; —SSi($R_7$)$_3$, wherein the $R_7$ groups are independently selected from an alkyl group having one to 16 carbon atoms and phenyl; —SCH$_2$(CH$_2$)$_c$O(CH$_2$(CH$_2$)$_c$O)$_d$R$_9$ or —SCH$_2$(CH$_2$)$_c$S—(CH$_2$(CH$_2$)$_c$O)$_d$R$_9$, wherein c is one or two, d is an integer from one to five, and R$_9$ is hydrogen or an alkyl group having one to 16 carbon atoms; —SCH$_2$(CH$_2$)$_c$E(CH$_2$(CH$_2$)$_c$F)$_d$R$_9$, wherein E and F are independently selected from the group consisting of selenium, tellurium, alkylamino wherein the alkyl group has one to 16 carbon atoms, alkyl wherein the alkyl group has two to ten carbon atoms, p-toluene-sulfonamide, 2-pyridylmethyl, COCH$_2$COR$_9$, CH$_2$COCH$_2$COR$_9$, CH$_2$CO$_2$H, and acetamide; trithiocarbonate; and —S—(CH$_2$—S)$_q$—, —S—(CH$_2$CH$_2$—S)$_q$—, or —S—(CH$_2$CH$_2$CH$_2$—S)$_q$—, wherein q is an integer from 2 through 6;

(b) an amino moiety, said amino moiety selected from the group consisting of

wherein R$_1$ and R$_2$ are independently selected from the group consistina of hydrogen, an alkyl group having one to 16 carbon atoms, 2-pyridylmethyl, benzyl, allyl, —CH$_2$CO$_2$H, —COCH$_2$OR$_{15}$, and —CH$_2$OCCH$_2$COR$_{15}$, wherein R$_{15}$ is an alkyl group having one to 16 carbon atoms; —NR$_{16}$—(CH$_2$)$_q$—NR$_{16}$—; —NR$_{16}$—(CH$_2$CH$_2$CH$_2$NR$_{16}$)$_q$—CH$_2$CH$_2$CH$_2$NR$_{16}$—; —NR$_{16}$—(CH$_2$—NR$_{16}$)$_q$—CH$_2$NR$_{16}$—; and —NR$_{16}$—(CH$_2$CH$_2$NR16)$_q$CH$_2$CH$_2$NR$_{16}$—, wherein q is an integer from 2 through 6, and R$_{16}$ is hydrogen, an alkyl group having one to ten carbon atoms, 2-pyridylmethyl, benzyl, allyl, —CH$_2$CO$_2$H, —COCH$_2$OR$_{10}$, or —CH$_2$OCCH$_2$—COR$_{10}$, wherein R$_{10}$ is an alkyl group having one to 12 carbon atoms;

(c) an oxo moiety, wherein said oxo moiety is selected from the group consisting of;

hydroxyl; alkoxy (—OR$_{17}$); acyloxy (—OCOR$_{17}$); silyloxy (—OSi(R$_{17}$)$_3$), wherein R$_{17}$ is an alkyl group having one to 12 carbon atoms, benzyl or phenyl; a ring containing at least two oxygen atoms; a ring containing at least one oxygen atom and either one nitrogen, sulfur, phosphorus, tellurium or selenium atom; carbonate; —O—((CH$_2$)$_t$—X)$_v$—O—, wherein X is sulfur, oxygen, phosphorus, selenium, tellurium, or —NR$_{11}$, wherein R$_{11}$ is selected from the group consisting of hydrogen, an alkyl group having one to six carbon atoms, 2-pyridylmethyl, benzyl, allyl, —CH$_2$CO$_2$H, —COCH$_2$OR$_{10}$, and —CH$_2$OCCH$_2$COR$_{10}$, wherein R$_{10}$ is an alkyl group having one to twelve carbon atoms, v is an integer 1 through 6, and t is an integer 1 through 3; and a ring having the structure

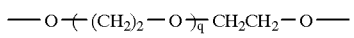

wherein q is an integer from 2 through 6, and wherein the oxygen atoms can be substituted, individually or collectively, with nitrogen, sulfur, phosphorus, tellurium or selenium;

(d) a phospho moiety, wherein the phospho moiety is selected from the group consisting of alkylphosphino (—PR$_3$R$_4$), wherein R$_3$ and R$_4$ can be the same or different and are alkyl groups having one to 12 carbon atoms, benzyl, phenyl, polyethyleneoxy or polyohenyl ether; a phosphonate ester (P(OR$_5$)$_2$, wherein R$_5$ is an alkyl group having 1 to 12 carbon atoms or phenyl;

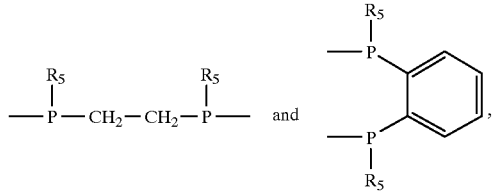

wherein R$_5$ is hydrogen, an alkyl croup having 1 to 3 carbon atoms or phenyl:

(e) a seleno moiety;

(f) a telluro moiety, wherein the seleno moiety or telluro moiety is selected from the group consisting of seleno (—SeH or —Se$^-$); telluro (—The or Te$^-$); alkylseleno; alkyltelluro (—Se(Te)R$_6$), wherein R$_6$ is an alkyl group having one to 12 carbon atoms, allyl, phenyl or benzyl; —Se(Te)M$^2$, wherein M$^2$ is an alkali metal ion or an alkaline earth metal ion; —Se(Te)Si(R$_7$)$_3$, wherein the R$_7$ groups are independently selected from an alkyl group having one to 12 carbon atoms and phenyl; —Se(Te)CH$_2$C$_6$H$_4$-4-CO$_2$R$_8$, R$_8$ is an alkyl group having one to six carbon atoms or phenyl: —Se(Te)CH$_2$(CH$_2$)$_c$O(CH$_2$(CH$_2$)$_c$O)$_d$R$_9$; —Se (Te)—CH$_2$(CH$_2$)$_c$S(CH$_2$(CH$_2$)$_c$O)$_d$R$_9$, wherein c is one or two, d is an integer from one to five, and R$_9$ is hydrogen or an alkyl group having one to 12 carbon atoms; and —Se(Te)CH$_2$—(CH$_2$)$_c$E(CH$_2$(CH$_2$)$_c$F)$_d$R$_9$, wherein E and F are independently selected from the group consisting of selenium, tellurium, alkylamino (wherein the alkyl group has one to five carbon atoms), alkyl (wherein the alkyl group has two to ten carbon atoms), 2-pyridylmethyl, —COCH$_2$COR$_9$, —CH$_2$COCH$_2$—COR$_9$, p-toluenesulfonamide and acetamide;

and (g) a hydrocarbon moiety, wherein the hydrocarbon moiety is selected from the group consisting of hydrogen; an alkyl group having one to 18 carbon atoms; phenyl; alkylphenyl; alkoxyphenyl, wherein the alkyl or alkoxy group has one to 12 carbon atoms; benzo; and polyethyleneoxyphenyl;

and wherein at least one of A, B, C, and D is capable of complexing with a metal ion M$^1$, wherein the hydrocarbon moieties are taken as a ring and are selected from the group consisting of an alkene, an alkyne, a strained alkene, and a diene.

31. The compound of claim 30 wherein the hydrocarbon moieties are selected from the group consisting of

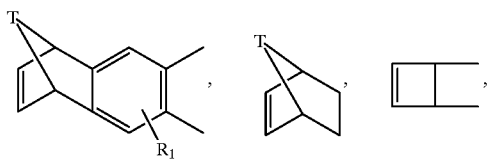

-continued

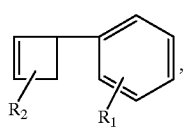 , 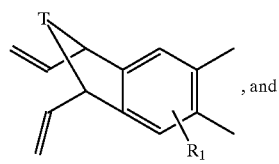 , and

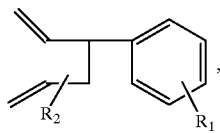 , wherein T is selected from the group consisting of O, S, $NR_{26}$, and $C(R_{26})_2$, wherein $R_{26}$ is selected, independently, from the group consisting of hydrogen, $C_1$–$C_4$ alkyl, $C_1$–$C_4$ alkoxy, and benzyl, and $R_1$ and $R_2$ are selected, independently, from the group consisting of hydrogen, an alkyl group having one to 16 carbon atoms, 2-pyridylmethyl, benzyl, allyl, $-CH_2CO_2H$, $-COCH_2OR_{15}$, and $-CH_2OCCH_2COR_{15}$.

32. The compound of claim 31 wherein the hydrocarbon moieties are selected from the group consisting of

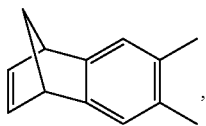 , 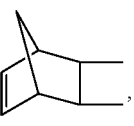 , 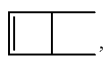 ,

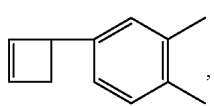 , 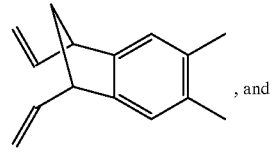 , and

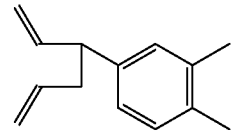 .

* * * * *

UNITED STATES PATENT AND TRADEMARK OFFICE
CERTIFICATE OF CORRECTION

PATENT NO.   :   5,912,341                                        Page 1 of 2

DATED        :   June 15, 1999

INVENTOR(S)  :   BRIAN M. HOFFMAN ET AL.

It is certified that error appears in the above-identified patent and that said Letters Patent is hereby corrected as shown below:

Column 52, line 6, "-((cH$_2$)..."
should be -- -((CH$_2$) ... --

Column 52, line 50, "Te." should be -- Te --

Column 55, line 10, insert the following
after the line beginning "wherein J is ... ."
-- -O$^-$, -OR$_{20}$, --

Column 55, line 15, insert the following
before the line beginning "wherein R$_{20}$ and . . .
-- -NHCH$_2$CO$_2^-$, -NH(CH$_2$)$_4$N$^+$(CH$_3$)$_3$, --

Column 56, line 33, insert the following
after the line beginning "J is . . ."
-- -O$^-$, -OR$_{20}$, --

Column 56 line 43, insert the following
before the line beginning "wherein R$_{20}$ and . . .
-- -NHCH$_2$CO$_2^-$, -NH(CH$_2$)$_4$N$^+$(CH$_3$)$_3$, --

Column 60, line 2, insert the following
after the line beginning "J is . . ."
-- -O$^-$, -OR$_{20}$, --

Column 60, line 8, insert the following
before the line beginning "wherein R$_{20}$ and . . .
-- -NHCH$_2$CO$_2^-$, -NH(CH$_2$)$_4$N$^+$(CH$_3$)$_3$, --

Column 61, line 16, insert the following
after the line beginning "J is . . ."
-- -O$^-$, -OR$_{20}$, --

UNITED STATES PATENT AND TRADEMARK OFFICE
CERTIFICATE OF CORRECTION

PATENT NO. : 5,912,341
DATED : June 15, 1999
INVENTOR(S) : BRIAN M. HOFFMAN ET AL.

It is certified that error appears in the above-identified patent and that said Letters Patent is hereby corrected as shown below:

Column 61, line 22, insert the following before the line beginning "wherein $R_{20}$ and . . .
-- $-NHCH_2CO_2^-$, $-NH(CH_2)_dN^+(CH_3)_3$, --

Column 63, line 45, between "and" and "integer" insert the following: -- p is an --

Column 65, line 41, "completing" should be --complexing--

Column 65, line 55, "$-SCH_2(CH_2)_2$" should be -- $-SCH_2(CH_2)_c$ --

Column 69, line 25, "consistina" should be --consisting--

Column 70, line 4, "polyohenyl" should be --polyphenyl--

Column 70, line 18, "croup" should be --group--

Signed and Sealed this

Second Day of May, 2000

Attest:

Q. TODD DICKINSON

*Attesting Officer*      *Director of Patents and Trademarks*